United States Patent
Minchiotti et al.

(10) Patent No.: US 7,638,330 B2
(45) Date of Patent: Dec. 29, 2009

(54) METHOD OF PROMOTING THE DIFFERENTIATION OF STAMINAL CELLS

(75) Inventors: Gabriella Minchiotti, Via Ugo Ricci, 19 IT - 80100 Napoli (IT); Maria Persico, Via Camillo de Nardis, 10, IT-80127 Napoli (IT); Silvia Parisi, Naples (IT)

(73) Assignees: Gabriella Minchiotti, Naples (IT); Maria Persico, Naples (IT)

( * ) Notice: Subject to any disclaimer, the term of this patent is extended or adjusted under 35 U.S.C. 154(b) by 527 days.

(21) Appl. No.: 10/550,498

(22) PCT Filed: Mar. 19, 2004

(86) PCT No.: PCT/IT2004/000133

§ 371 (c)(1),
(2), (4) Date: Nov. 21, 2005

(87) PCT Pub. No.: WO2004/083375

PCT Pub. Date: Sep. 30, 2004

(65) Prior Publication Data

US 2008/0159989 A1  Jul. 3, 2008

(30) Foreign Application Priority Data

Mar. 21, 2003 (IT) .......................... RM2003A0125
Jul. 29, 2003 (IT) .......................... RM2003A0370

(51) Int. Cl.
*C12N 5/06* (2006.01)
*A61K 35/34* (2006.01)
*A61K 38/18* (2006.01)

(52) U.S. Cl. ...................................... 435/377; 435/365
(58) Field of Classification Search ...................... None
See application file for complete search history.

(56) References Cited

FOREIGN PATENT DOCUMENTS

| WO | WO 01/68814 A2 | 9/2001 |
|----|----------------|--------|
| WO | WO 02/26941 A2 | 4/2002 |
| WO | WO 2004/053084 A2 | 6/2004 |

OTHER PUBLICATIONS

PCT International Search Report for Minchiotti, et al., Int'l Application No. PCT/IT04/000133, Filed Mar. 19, 2004, Dated Sep. 2, 2004.
Piccolo, et al., "The head inducer Cerberus is a multifunctional antagonist of Nodal, BMP and Wnt signals", Nature, vol. 397, No. 6721, pp. 707-710 (1999).
Parisi, et al., "Nodal-dependent Cripto signaling promotes cardiomyogenesis and redirects the neural fate of embryonic stem cells", Journal of Cell Biology, vol. 163, No. 2, pp. 303-314 (2003).
Adamson, et al., "Cripto: A tumor growth factor and more", Journal of Cellular Physiology, vol. 190, No. 3, pp. 267-278 (2002).
Xu, et al., "Specific arrest of cardioegensis in cultured embryonic stem cells lacking Cripto-1", Developmental Biology, vol. 196, No. 2, pp. 237-247 (1998).
Baldassarre, et al, "Transfection with a Cripto anti-sense plasmid suppresses endogenous Cripto expression and inhibits transformation in a human embryonal carcinoma cell line", International Journal of Cancer, vol. 66, No. 4, pp. 538-543 (1996).

*Primary Examiner*—Daniel C Gamett
(74) *Attorney, Agent, or Firm*—Law Offices of Albert Wai-Kit Chan, PLLC

(57) ABSTRACT

A method is described by which stem cells are induced to differentiate into cardiomycocytes; the method comprises exposure for a length of time and at efficacious quantities of a protein of the EGF-CFC family or its derivatives having at least the EGE and CFC domains; or to differentiate into neuronal cells, comprising the exposure to Cripto protein inhibitors. Compositions are described for therapeutic use in treating heart disorders, comprising a therapeutically efficacious quantity of a protein or its derivatives having at least the EGF and CFC domains of a protein of the EGF-CFC family.

4 Claims, 8 Drawing Sheets

Figure 1:
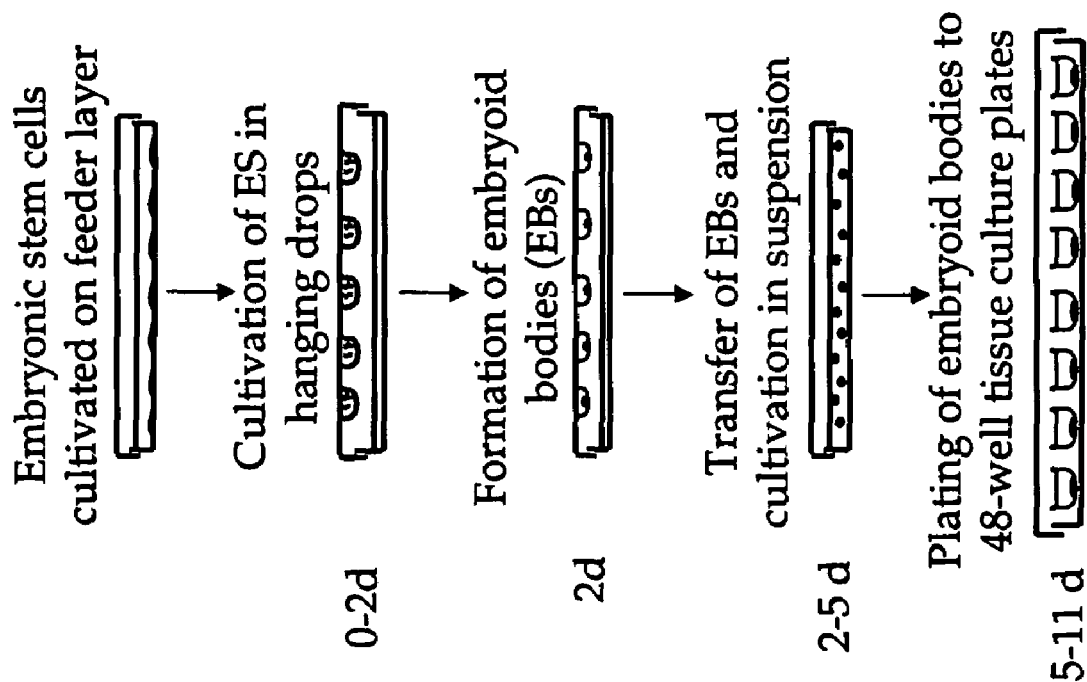

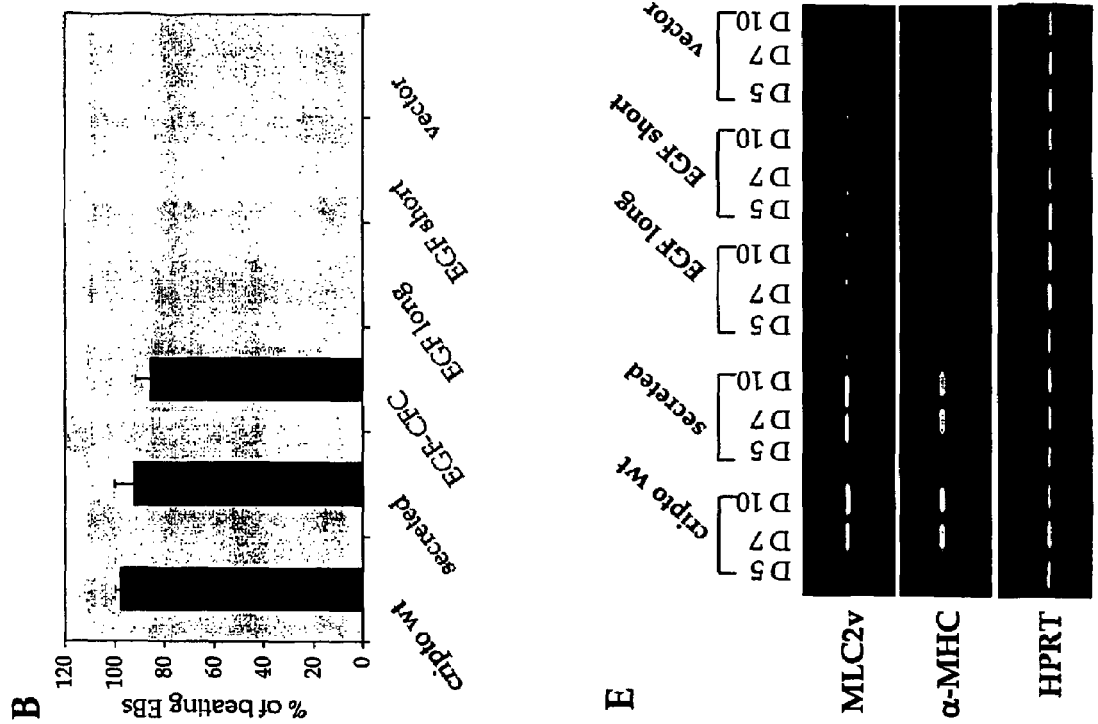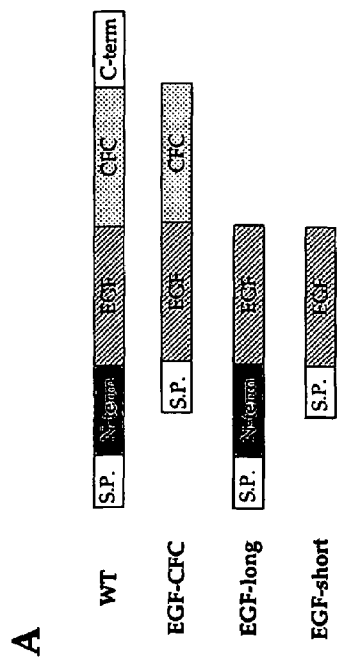
Fig. 2

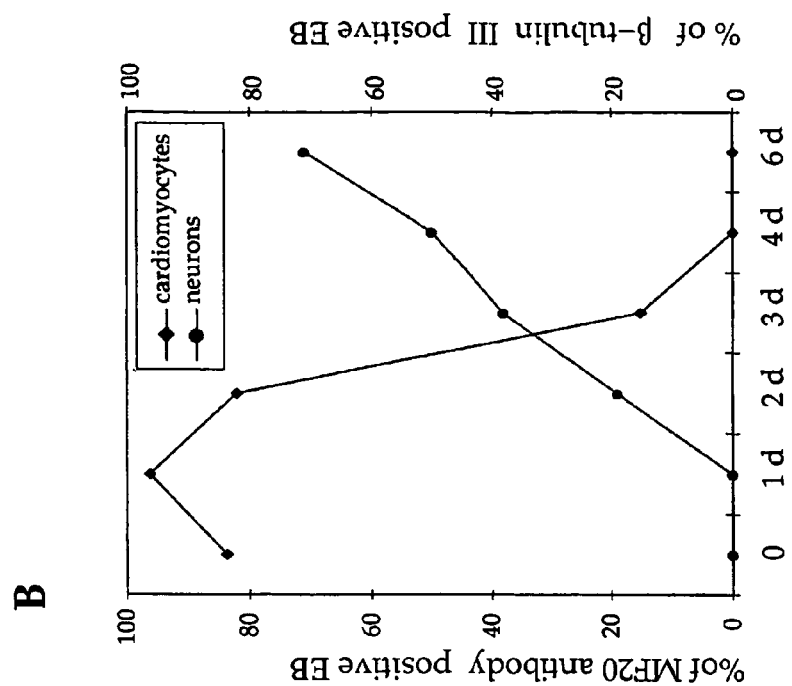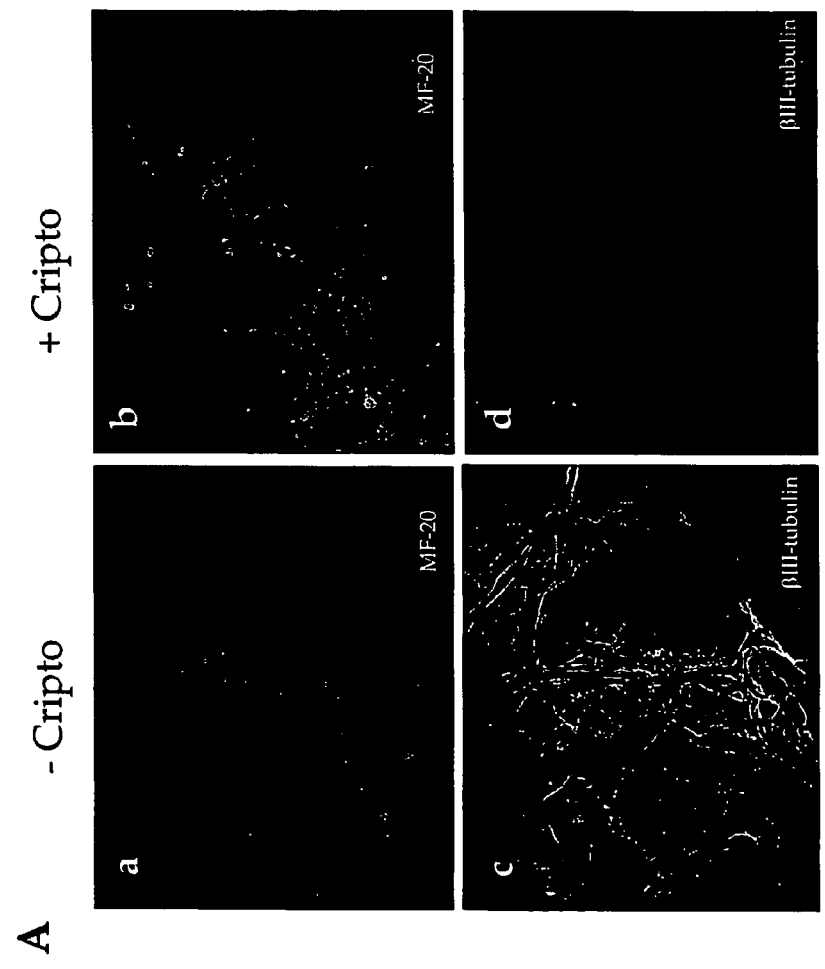
Fig. 8

SEQUENCE LISTING

```
<160> NUMBER OF SEQ ID NOS: 42

<210> SEQ ID NO 1
<211> LENGTH: 22
<212> TYPE: DNA
<213> ORGANISM: Artificial
<220> FEATURE:
<223> OTHER INFORMATION: primer nodal F
<220> FEATURE:
<221> NAME/KEY: primer_bind
<222> LOCATION: (1)..(22)

<400> SEQUENCE: 1
ttccttctca ggtcacgttt gc                                              22

<210> SEQ ID NO 2
<211> LENGTH: 21
<212> TYPE: DNA
<213> ORGANISM: Artificial
<220> FEATURE:
<223> OTHER INFORMATION: Primer nodal R
<220> FEATURE:
<221> NAME/KEY: primer_bind
<222> LOCATION: (1)..(21)

<400> SEQUENCE: 2
ggtggggttg gtatcgtttc a                                               21

<210> SEQ ID NO 3
<211> LENGTH: 25
<212> TYPE: DNA
<213> ORGANISM: Artificial
<220> FEATURE:
<223> OTHER INFORMATION: primer alk-4 F
<220> FEATURE:
<221> NAME/KEY: primer_bind
<222> LOCATION: (1)..(25)

<400> SEQUENCE: 3
aaggatccag gctctgctgt gtgcc                                           25

<210> SEQ ID NO 4
<211> LENGTH: 26
<212> TYPE: DNA
<213> ORGANISM: Artificial
<220> FEATURE:
<223> OTHER INFORMATION: primer alk-4 R
<220> FEATURE:
```

```
<221> NAME/KEY: primer_bind
<222> LOCATION: (1)..(26)

<400> SEQUENCE: 4
acggatccat gtccaacctc tggcgg                                            26

<210> SEQ ID NO 5
<211> LENGTH: 20
<212> TYPE: DNA
<213> ORGANISM: Artificial
<220> FEATURE:
<223> OTHER INFORMATION: primer ActRIIB F
<220> FEATURE:
<221> NAME/KEY: primer_bind
<222> LOCATION: (1)..(20)

<400> SEQUENCE: 5
atgtgccgtg gtgtcgtggt                                                   20

<210> SEQ ID NO 6
<211> LENGTH: 20
<212> TYPE: DNA
<213> ORGANISM: Artificial
<220> FEATURE:
<223> OTHER INFORMATION: primer ActRIIB R
<220> FEATURE:
<221> NAME/KEY: primer_bind
<222> LOCATION: (1)..(20)

<400> SEQUENCE: 6
gacctcctga tcagggatac                                                   20

<210> SEQ ID NO 7
<211> LENGTH: 24
<212> TYPE: DNA
<213> ORGANISM: Artificial
<220> FEATURE:
<223> OTHER INFORMATION: primer MLC2v F
<220> FEATURE:
<221> NAME/KEY: primer_bind
<222> LOCATION: (1)..(24)

<400> SEQUENCE: 7
gccaagaagc ggatagaagg cggg                                              24

<210> SEQ ID NO 8
<211> LENGTH: 24
<212> TYPE: DNA
<213> ORGANISM: Artificial
<220> FEATURE:
<223> OTHER INFORMATION: primer MLC2v R
<220> FEATURE:
<221> NAME/KEY: primer_bind
<222> LOCATION: (1)..(24)

<400> SEQUENCE: 8
ctgtggttca gggctcagtc cttc                                              24

<210> SEQ ID NO 9
<211> LENGTH: 24
<212> TYPE: DNA
<213> ORGANISM: Artificial
<220> FEATURE:
<223> OTHER INFORMATION: primer cardiac alphaMHC F
<220> FEATURE:
<221> NAME/KEY: primer_bind
<222> LOCATION: (1)..(24)

<400> SEQUENCE: 9
```

-continued ggaagagtga gcggcgcatc aagg                                              24

<210> SEQ ID NO 10
<211> LENGTH: 22
<212> TYPE: DNA
<213> ORGANISM: Artificial
<220> FEATURE:
<223> OTHER INFORMATION: primer cardiac alphaMHC R
<220> FEATURE:
<221> NAME/KEY: primer_bind
<222> LOCATION: (1)..(22)

<400> SEQUENCE: 10
ctgctggaga ggttattcct cg                                                22

<210> SEQ ID NO 11
<211> LENGTH: 25
<212> TYPE: DNA
<213> ORGANISM: Artificial
<220> FEATURE:
<223> OTHER INFORMATION: primer HPRT F
<220> FEATURE:
<221> NAME/KEY: primer_bind
<222> LOCATION: (1)..(25)

<400> SEQUENCE: 11
cctgctggat tacattaaag cactg                                             25

<210> SEQ ID NO 12
<211> LENGTH: 25
<212> TYPE: DNA
<213> ORGANISM: Artificial
<220> FEATURE:
<223> OTHER INFORMATION: primer HPRT R
<220> FEATURE:
<221> NAME/KEY: primer_bind
<222> LOCATION: (1)..(25)

<400> SEQUENCE: 12
cctgaagtac tcattatagt caagg                                             25

<210> SEQ ID NO 13
<211> LENGTH: 27
<212> TYPE: DNA
<213> ORGANISM: Artificial
<220> FEATURE:
<223> OTHER INFORMATION: Synthetic mut Asn63-Ile
<220> FEATURE:
<221> NAME/KEY: primer_bind
<222> LOCATION: (1)..(27)

<400> SEQUENCE: 13
gtaagtcgct tattaaaact tgctgtc                                           27

<210> SEQ ID NO 14
<211> LENGTH: 27
<212> TYPE: DNA
<213> ORGANISM: Artificial
<220> FEATURE:
<223> OTHER INFORMATION: Synthetic mut Asn63-Ile
<220> FEATURE:
<221> NAME/KEY: primer_bind
<222> LOCATION: (1)..(27)

<400> SEQUENCE: 14
gacagcaagt tttaataagc gacttac                                           27

```
<210> SEQ ID NO 15
<211> LENGTH: 38
<212> TYPE: DNA
<213> ORGANISM: Artificial
<220> FEATURE:
<223> OTHER INFORMATION: Synthetic mut Gly71-Asn
<220> FEATURE:
<221> NAME/KEY: primer_bind
<222> LOCATION: (1)..(38)

<400> SEQUENCE: 15
cttgctgtct gaatggaaac acttgcatcc tggggtcc                              38

<210> SEQ ID NO 16
<211> LENGTH: 38
<212> TYPE: DNA
<213> ORGANISM: Artificial
<220> FEATURE:
<223> OTHER INFORMATION: Synthetic mut Gly71-Asn
<220> FEATURE:
<221> NAME/KEY: primer_bind
<222> LOCATION: (1)..(38)

<400> SEQUENCE: 16
ggaccccagg atgcaagtgt ttccattcag acagcaag                              38

<210> SEQ ID NO 17
<211> LENGTH: 23
<212> TYPE: DNA
<213> ORGANISM: Artificial
<220> FEATURE:
<223> OTHER INFORMATION: Synthetic mut Thr72-Ala
<220> FEATURE:
<221> NAME/KEY: primer_bind
<222> LOCATION: (1)..(23)

<400> SEQUENCE: 17
gaatggaggg gcttgcatcc tgg                                              23

<210> SEQ ID NO 18
<211> LENGTH: 23
<212> TYPE: DNA
<213> ORGANISM: Artificial
<220> FEATURE:
<223> OTHER INFORMATION: Synthetic mut Thr72-Ala
<220> FEATURE:
<221> NAME/KEY: primer_bind
<222> LOCATION: (1)..(23)

<400> SEQUENCE: 18
ccaggatgca agcccctcca ttc                                              23

<210> SEQ ID NO 19
<211> LENGTH: 29
<212> TYPE: DNA
<213> ORGANISM: Artificial
<220> FEATURE:
<223> OTHER INFORMATION: Synthetic mut Ser77-Ala
<220> FEATURE:
<221> NAME/KEY: primer_bind
<222> LOCATION: (1)..(29)

<400> SEQUENCE: 19
cttgcatcct gggggccttc tgtgcctgc                                        29

<210> SEQ ID NO 20
<211> LENGTH: 29
<212> TYPE: DNA
<213> ORGANISM: Artificial
```

```
<220> FEATURE:
<223> OTHER INFORMATION: Synthetic mut Ser77-Ala
<220> FEATURE:
<221> NAME/KEY: primer_bind
<222> LOCATION: (1)..(29)

<400> SEQUENCE: 20
gcaggcacag aaggccccca ggatgcaag                                    29

<210> SEQ ID NO 21
<211> LENGTH: 31
<212> TYPE: DNA
<213> ORGANISM: Artificial
<220> FEATURE:
<223> OTHER INFORMATION: Synthetic mut Phe78-Ala
<220> FEATURE:
<221> NAME/KEY: primer_bind
<222> LOCATION: (1)..(31)

<400> SEQUENCE: 21
gcatcctggg gtccgcctgt gcctgccctc c                                 31

<210> SEQ ID NO 22
<211> LENGTH: 31
<212> TYPE: DNA
<213> ORGANISM: Artificial
<220> FEATURE:
<223> OTHER INFORMATION: Synthetic mut Phe78-Ala
<220> FEATURE:
<221> NAME/KEY: primer_bind
<222> LOCATION: (1)..(31)

<400> SEQUENCE: 22
gcatcctggg gtccgcctgt gcctgccctc c                                 31

<210> SEQ ID NO 23
<211> LENGTH: 31
<212> TYPE: DNA
<213> ORGANISM: Artificial
<220> FEATURE:
<223> OTHER INFORMATION: Synthetic mut Phe78-Trp
<220> FEATURE:
<221> NAME/KEY: primer_bind
<222> LOCATION: (1)..(31)

<400> SEQUENCE: 23
gcatcctggg gtcctggtgt gcctgccctc c                                 31

<210> SEQ ID NO 24
<211> LENGTH: 31
<212> TYPE: DNA
<213> ORGANISM: Artificial
<220> FEATURE:
<223> OTHER INFORMATION: Synthetic mut Phe78-Trp
<220> FEATURE:
<221> NAME/KEY: primer_bind
<222> LOCATION: (1)..(31)

<400> SEQUENCE: 24
ggagggcagg cacaccagga ccccaggatg c                                 31

<210> SEQ ID NO 25
<211> LENGTH: 32
<212> TYPE: DNA
<213> ORGANISM: Artificial
<220> FEATURE:
<223> OTHER INFORMATION: Synthetic mut His104-Ala
<220> FEATURE:
<221> NAME/KEY: primer_bind
```

<222> LOCATION: (1)..(32)

<400> SEQUENCE: 25
gtgggtctat cctcgctggc acctggctgc cc                32

<210> SEQ ID NO 26
<211> LENGTH: 32
<212> TYPE: DNA
<213> ORGANISM: Artificial
<220> FEATURE:
<223> OTHER INFORMATION: Synthetic mut His104-Ala
<220> FEATURE:
<221> NAME/KEY: primer_bind
<222> LOCATION: (1)..(32)

<400> SEQUENCE: 26
gggcagccag gtgccagcga ggatagaccc ac                32

<210> SEQ ID NO 27
<211> LENGTH: 21
<212> TYPE: DNA
<213> ORGANISM: Artificial
<220> FEATURE:
<223> OTHER INFORMATION: Synthetic mut Trp107-Gly
<220> FEATURE:
<221> NAME/KEY: primer_bind
<222> LOCATION: (1)..(21)

<400> SEQUENCE: 27
catggcaccg ggctgcccaa g                            21

<210> SEQ ID NO 28
<211> LENGTH: 21
<212> TYPE: DNA
<213> ORGANISM: Artificial
<220> FEATURE:
<223> OTHER INFORMATION: Synthetic mut Trp107-Gly
<220> FEATURE:
<221> NAME/KEY: primer_bind
<222> LOCATION: (1)..(21)

<400> SEQUENCE: 28
cttgggcagc ccggtgccat g                            21

<210> SEQ ID NO 29
<211> LENGTH: 31
<212> TYPE: DNA
<213> ORGANISM: Artificial
<220> FEATURE:
<223> OTHER INFORMATION: Synthetic mut Arg116-Ala
<220> FEATURE:
<221> NAME/KEY: primer_bind
<222> LOCATION: (1)..(31)

<400> SEQUENCE: 29
gtgttccctg tgcgcatgct ggcacggcca g                 31

<210> SEQ ID NO 30
<211> LENGTH: 31
<212> TYPE: DNA
<213> ORGANISM: Artificial
<220> FEATURE:
<223> OTHER INFORMATION: Synthetic mut Arg116-Ala
<220> FEATURE:
<221> NAME/KEY: primer_bind
<222> LOCATION: (1)..(31)

<400> SEQUENCE: 30
ctggccgtgc cagcatgcgc acagggaaca c                    31

<210> SEQ ID NO 31
<211> LENGTH: 32
<212> TYPE: DNA
<213> ORGANISM: Artificial
<220> FEATURE:
<223> OTHER INFORMATION: Synthetic mut Leu122-Asn
<220> FEATURE:
<221> NAME/KEY: primer_bind
<222> LOCATION: (1)..(32)

<400> SEQUENCE: 31
gctggcacgg ccagaaccac tgtcttcctc ag                  32

<210> SEQ ID NO 32
<211> LENGTH: 32
<212> TYPE: DNA
<213> ORGANISM: Artificial
<220> FEATURE:
<223> OTHER INFORMATION: Synthetic mut Leu122-Asn
<220> FEATURE:
<221> NAME/KEY: primer_bind
<222> LOCATION: (1)..(32)

<400> SEQUENCE: 32
ctgaggaaga cagtggttct ggccgtgcca gc                  32

<210> SEQ ID NO 33
<211> LENGTH: 171
<212> TYPE: PRT
<213> ORGANISM: Artificial
<220> FEATURE:
<223> OTHER INFORMATION: Synthetic m cripto
<220> FEATURE:
<221> NAME/KEY: VARIANT
<222> LOCATION: (1)..(171)

<400> SEQUENCE: 33

Met Gly Tyr Phe Ser Ser Val Val Leu Leu Val Ala Ile Ser Ser
1               5                   10                  15

Ala Phe Glu Phe Gly Pro Val Ala Gly Arg Asp Leu Ala Ile Arg Asp
            20                  25                  30

Asn Ser Ile Trp Asp Gln Lys Glu Pro Ala Val Arg Asp Arg Ser Phe
35                  40                  45

Gln Phe Val Pro Ser Val Gly Ile Gln Asn Ser Lys Ser Leu Asn Lys
50                  55                  60

Thr Cys Cys Leu Asn Gly Gly Thr Cys Ile Leu Gly Ser Phe Cys Ala
65                  70                  75                  80

Cys Pro Pro Ser Phe Tyr Gly Arg Asn Cys Glu His Asp Val Arg Lys
                85                  90                  95

Glu His Cys Gly Ser Ile Leu His Gly Thr Trp Leu Pro Lys Lys Cys
            100                 105                 110

Ser Leu Cys Arg Cys Trp His Gly Gln Leu His Cys Leu Pro Gln Thr
115                 120                 125

Phe Leu Pro Gly Cys Asp Gly His Val Met Asp Gln Asp Leu Lys Ala
130                 135                 140

Ser Arg Thr Pro Cys Gln Thr Pro Ser Val Thr Thr Thr Phe Met Leu
145                 150                 155                 160

Ala Gly Ala Cys Leu Phe Leu Asp Met Lys Val
                165                 170

```
<210> SEQ ID NO 34
<211> LENGTH: 156
<212> TYPE: PRT
<213> ORGANISM: Artificial
<220> FEATURE:
<223> OTHER INFORMATION: Synthetic secreted m cripto
<220> FEATURE:
<221> NAME/KEY: VARIANT
<222> LOCATION: (1)..(156)

<400> SEQUENCE: 34

Met Gly Tyr Phe Ser Ser Val Val Leu Leu Val Ala Ile Ser Ser
1               5                   10                  15

Ala Phe Glu Phe Gly Pro Val Ala Gly Arg Asp Leu Ala Ile Arg Asp
            20                  25                  30

Asn Ser Ile Trp Asp Gln Lys Glu Pro Ala Val Arg Asp Arg Ser Phe
        35                  40                  45

Gln Phe Val Pro Ser Val Gly Ile Gln Asn Ser Lys Ser Leu Asn Lys
    50                  55                  60

Thr Cys Cys Leu Asn Gly Gly Thr Cys Ile Leu Gly Ser Phe Cys Ala
65                  70                  75                  80

Cys Pro Pro Ser Phe Tyr Gly Arg Asn Cys Glu His Asp Val Arg Lys
                85                  90                  95

Glu His Cys Gly Ser Ile Leu His Gly Thr Trp Leu Pro Lys Lys Cys
            100                 105                 110

Ser Leu Cys Arg Cys Trp His Gly Gln Leu His Cys Leu Pro Gln Thr
        115                 120                 125

Phe Leu Pro Gly Cys Asp Gly His Val Met Asp Gln Asp Leu Lys Ala
    130                 135                 140

Ser Arg Thr Pro Cys Gln Thr Pro Ser Val Thr Thr
145                 150                 155

<210> SEQ ID NO 35
<211> LENGTH: 166
<212> TYPE: PRT
<213> ORGANISM: Artificial
<220> FEATURE:
<223> OTHER INFORMATION: Synthetic m cripto His
<220> FEATURE:
<221> NAME/KEY: VARIANT
<222> LOCATION: (1)..(166)

<400> SEQUENCE: 35

Met Gly Tyr Phe Ser Ser Val Val Leu Leu Val Ala Ile Ser Ser
1               5                   10                  15

Ala Phe Glu Phe Gly Pro Val Ala Gly Arg Asp Leu Ala Ile Arg Asp
            20                  25                  30

Asn Ser Ile Trp Asp Gln Lys Glu Pro Ala Val Arg Asp Arg Ser Phe
        35                  40                  45

Gln Phe Val Pro Ser Val Gly Ile Gln Asn Ser Lys Ser Leu Asn Lys
    50                  55                  60

Thr Cys Cys Leu Asn Gly Gly Thr Cys Ile Leu Gly Ser Phe Cys Ala
65                  70                  75                  80

Cys Pro Pro Ser Phe Tyr Gly Arg Asn Cys Glu His Asp Val Arg Lys
                85                  90                  95

Glu His Cys Gly Ser Ile Leu His Gly Thr Trp Leu Pro Lys Lys Cys
            100                 105                 110

Ser Leu Cys Arg Cys Trp His Gly Gln Leu His Cys Leu Pro Gln Thr
        115                 120                 125
```

```
Phe Leu Pro Gly Cys Asp Gly His Val Met Asp Gln Asp Leu Lys Ala
130                 135                 140

Ser Arg Thr Pro Cys Gln Thr Pro Ser Val Thr Thr Thr Asn Ser Gly
145                 150                 155                 160

His His His His His His
165

<210> SEQ ID NO 36
<211> LENGTH: 129
<212> TYPE: PRT
<213> ORGANISM: Artificial
<220> FEATURE:
<223> OTHER INFORMATION: Synthetic EGF-CFC m cripto
<220> FEATURE:
<221> NAME/KEY: VARIANT
<222> LOCATION: (1)..(129)

<400> SEQUENCE: 36

Met Gly Tyr Phe Ser Ser Val Val Leu Leu Val Ala Ile Ser Ser
1               5                  10                  15

Ala Phe Glu Phe Gly Pro Val Ala Gly Ser Val Gly Ile Gln Asn Ser
20                  25                  30

Lys Ser Leu Asn Lys Thr Cys Cys Leu Asn Gly Gly Thr Cys Ile Leu
35                  40                  45

Gly Ser Phe Cys Ala Cys Pro Pro Ser Phe Tyr Gly Arg Asn Cys Glu
50                  55                  60

His Asp Val Arg Lys Glu His Cys Gly Ser Ile Leu His Gly Thr Trp
65                  70                  75                  80

Leu Pro Lys Lys Cys Ser Leu Cys Arg Cys Trp His Gly Gln Leu His
85                  90                  95

Cys Leu Pro Gln Thr Phe Leu Pro Gly Cys Asp Gly His Val Met Asp
100                 105                 110

Gln Asp Leu Lys Ala Ser Arg Thr Pro Cys Gln Thr Pro Ser Val Thr
115                 120                 125

Thr

<210> SEQ ID NO 37
<211> LENGTH: 139
<212> TYPE: PRT
<213> ORGANISM: Artificial
<220> FEATURE:
<223> OTHER INFORMATION: Synthetic EGF-CFC m cripto His
<220> FEATURE:
<221> NAME/KEY: VARIANT
<222> LOCATION: (1)..(139)

<400> SEQUENCE: 37

Met Gly Tyr Phe Ser Ser Val Val Leu Leu Val Ala Ile Ser Ser
1               5                  10                  15

Ala Phe Glu Phe Gly Pro Val Ala Gly Ser Val Gly Ile Gln Asn Ser
20                  25                  30

Lys Ser Leu Asn Lys Thr Cys Cys Leu Asn Gly Gly Thr Cys Ile Leu
35                  40                  45

Gly Ser Phe Cys Ala Cys Pro Pro Ser Phe Tyr Gly Arg Asn Cys Glu
50                  55                  60

His Asp Val Arg Lys Glu His Cys Gly Ser Ile Leu His Gly Thr Trp
65                  70                  75                  80

Leu Pro Lys Lys Cys Ser Leu Cys Arg Cys Trp His Gly Gln Leu His
85                  90                  95
```

Cys Leu Pro Gln Thr Phe Leu Pro Gly Cys Asp Gly His Val Met Asp
100                 105                 110

Gln Asp Leu Lys Ala Ser Arg Thr Pro Cys Gln Thr Pro Ser Val Thr
115                 120                 125

Thr Thr Asn Ser Gly His His His His His His
130                 135

<210> SEQ ID NO 38
<211> LENGTH: 69
<212> TYPE: PRT
<213> ORGANISM: Artificial
<220> FEATURE:
<223> OTHER INFORMATION: Synthetic EGF short m cripto
<220> FEATURE:
<221> NAME/KEY: VARIANT
<222> LOCATION: (1)..(69)

<400> SEQUENCE: 38

Met Gly Tyr Phe Ser Ser Val Val Leu Leu Val Ala Ile Ser Ser
1               5                   10                  15

Ala Phe Glu Phe Gly Pro Val Ala Gly Ser Val Gly Ile Gln Asn Ser
20                  25                  30

Lys Ser Leu Asn Lys Thr Cys Cys Leu Asn Gly Gly Thr Cys Ile Leu
35                  40                  45

Gly Ser Phe Cys Ala Cys Pro Pro Ser Phe Tyr Gly Arg Asn Cys Glu
50                  55                  60

His Asp Val Arg Lys
65

<210> SEQ ID NO 39
<211> LENGTH: 96
<212> TYPE: PRT
<213> ORGANISM: Artificial
<220> FEATURE:
<223> OTHER INFORMATION: Synthetic EGF long m cripto
<220> FEATURE:
<221> NAME/KEY: VARIANT
<222> LOCATION: (1)..(96)

<400> SEQUENCE: 39

Met Gly Tyr Phe Ser Ser Val Val Leu Leu Val Ala Ile Ser Ser
1               5                   10                  15

Ala Phe Glu Phe Gly Pro Val Ala Gly Arg Asp Leu Ala Ile Arg Asp
20                  25                  30

Asn Ser Ile Trp Asp Gln Lys Glu Pro Ala Val Arg Asp Arg Ser Phe
35                  40                  45

Gln Phe Val Pro Ser Val Gly Ile Gln Asn Ser Lys Ser Leu Asn Lys
50                  55                  60

Thr Cys Cys Leu Asn Gly Gly Thr Cys Ile Leu Gly Ser Phe Cys Ala
65                  70                  75                  80

Cys Pro Pro Ser Phe Tyr Gly Arg Asn Cys Glu His Asp Val Arg Lys
85                  90                  95

<210> SEQ ID NO 40
<211> LENGTH: 188
<212> TYPE: PRT
<213> ORGANISM: Artificial
<220> FEATURE:
<223> OTHER INFORMATION: Synthetic h cripto
<220> FEATURE:
<221> NAME/KEY: VARIANT
<222> LOCATION: (1)..(188)

<400> SEQUENCE: 40

```
Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
            85                  90                  95

Cys Pro Pro Ser Phe Tyr Gly Arg Asn Cys Glu His Asp Val Arg Lys
        100                 105                 110

Glu Asn Cys Gly Ser Val Pro His Asp Thr Trp Leu Pro Lys Lys Cys
    115                 120                 125

Ser Leu Cys Lys Cys Trp His Gly Gln Leu Arg Cys Phe Pro Gln Ala
130                 135                 140

Phe Leu Pro Gly Cys Asp Gly Leu Val Met Asp Glu His Leu Val Ala
            145                 150                 155             160

Ser Arg Thr Pro Glu Leu Pro Pro Ser Ala Arg Thr Thr Thr Phe Met
        165                 170                 175

Leu Val Gly Ala Cys Leu Phe Leu Asp Met Lys Val
    180                 185
```

<210> SEQ ID NO 41
<211> LENGTH: 173
<212> TYPE: PRT
<213> ORGANISM: Artificial
<220> FEATURE:
<223> OTHER INFORMATION: Synthetic h cripto secreted
<220> FEATURE:
<221> NAME/KEY: VARIANT
<222> LOCATION: (1)..(173)

<400> SEQUENCE: 41

```
Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
            85                  90                  95

Cys Pro Pro Ser Phe Tyr Gly Arg Asn Cys Glu His Asp Val Arg Lys
        100                 105                 110

Glu Asn Cys Gly Ser Val Pro His Asp Thr Trp Leu Pro Lys Lys Cys
    115                 120                 125

Ser Leu Cys Lys Cys Trp His Gly Gln Leu Arg Cys Phe Pro Gln Ala
130                 135                 140

Phe Leu Pro Gly Cys Asp Gly Leu Val Met Asp Glu His Leu Val Ala
```

```
                            145                 150                 155                 160
Ser Arg Thr Pro Glu Leu Pro Pro Ser Ala Arg Thr Thr
165                 170

<210> SEQ ID NO 42
<211> LENGTH: 183
<212> TYPE: PRT
<213> ORGANISM: Artificial
<220> FEATURE:
<223> OTHER INFORMATION: Synthetic h cripto secreted His
<220> FEATURE:
<221> NAME/KEY: VARIANT
<222> LOCATION: (1)..(183)

<400> SEQUENCE: 42

Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
            85                  90                  95

Cys Pro Pro Ser Phe Tyr Gly Arg Asn Cys Glu His Asp Val Arg Lys
        100                 105                 110

Glu Asn Cys Gly Ser Val Pro His Asp Thr Trp Leu Pro Lys Lys Cys
    115                 120                 125

Ser Leu Cys Lys Cys Trp His Gly Gln Leu Arg Cys Phe Pro Gln Ala
130                 135                 140

Phe Leu Pro Gly Cys Asp Gly Leu Val Met Asp Glu His Leu Val Ala
            145                 150                 155                 160

Ser Arg Thr Pro Glu Leu Pro Pro Ser Ala Arg Thr Thr Thr Asn Ser
165                 170                 175

Gly His His His His His His
180
```

METHOD OF PROMOTING THE DIFFERENTIATION OF STAMINAL CELLS

This application is a National Stage Application of International Application No. PCT/IT2004/000133, filed Mar. 19, 2004, which claims priority of Italian Application No. RM2003A000125, filed Mar. 21, 2003 and Italian Application No. RM2003A000370, filed Jul. 29, 2003, the contents of the preceding applications are incorporated by reference into this application.

FIELD OF THE INVENTION

The invention concerns a method to promote stem cell differentiation. In particular, the invention is a method that uses the Cripto protein or its analogues or functional derivatives or inhibitors to induce stem cell differentiation into different lineages, such as cardiomyocytes or neuronal cells. Within the scope of the invention, the stem cells comprise both embryonal stem (ES) cells and derivatives from nonembryonal tissues. The EGF-CFC protein family (comprising Cripto, both human and mouse, chick, cryptic, oep, FRL-1 [Minchiotti et al., 2001] completely incorporated as reference) is involved in the embryonal development of vertebrates (Ding et al., 1998; Xu et al., 1999). Cripto is a molecular marker of undifferentiated ES cells in mice (Minchiotti et al., 2000) and human beings (Brivanlou et al., 2003).

DESCRIPTION OF THE INVENTION

The authors of the present invention have investigated the role Cripto plays in modulating differentiation, particularly in cardiomyogenesis and in neuronal cell induction. The authors found that the timing of initiation and the duration of Cripto signaling are essential for inducing the differentiation of ES cells into cardiomyocytes, indicating that Cripto acts during an early phase. However, Cripto seems to inhibit differentiation to the neuronal lineage. The authors have also reported that Cripto induction activates an intracellular protein that acts as a transducer in extracellular signaling, Smad2 (Adamson et al., 2002), and that the overexpression of the activated forms of type I Alk4 receptor compensates for the lack of Cripto signaling. Both the EGF-CFC domains are necessary for cardiomyogenesis, whereas they inhibit neuronal differentiation.

The invention may be advantageously applied as a stimulator of stem cells for transplants in the treatment of degenerative diseases such as myocardial infarction (Min JY et al., 2002). As is known, the adult heart has a limited regeneration capacity, so that any significant cell loss, as occurs during extensive cardiac infarction, is irreversible and can lead to a progressive deterioration of heart function and the development of heart failure (Gepstein et al., 2002). Both human and mouse ES cells differentiate spontaneously in vitro into cardiomyocytes when an embryoid body (EB) technique is applied; however, the specific biochemical stimuli for this process are unknown. Furthermore, cardiomyocytes represent only a minority of the EB cell population. The introduction of control genes in the development of stem cells represents an advantageous strategy to direct their differentiation, despite the various undesired side effects resulting from clonal variation, dependence on the primer and the ability of some stem cells to suppress the expression of ectopically transgenes expressed (Boehler et al., 2002).

The invention may be advantageously applied as a method to treat stem cells for use in transplants for neurodegenerative diseases such as Parkinson's disease, Alzheimer's disease, retinal degeneration, etc. Hence, ES cells constitute a nearly unlimited source of cells for cell therapy in treating degenerative diseases (Hynes and Rosenthal, 2000; Liu et al., 2000; Min et al., 2002; Svendsen and Smith, 1999). It is known, in fact, that ES cells can proliferate and differentiate in all types of an organism's cells. A recent report has indicated that ES cells are optimal candidates for cell therapy for neurodegenerative diseases since they can produce appropriate cell types when primed in vivo (Bjorklund et al., 2002; Arenas, 2002; Hara et al., 2004). In this context, it is crucial to develop experimental methods to prime cell differentiation starting with undifferentiated ES cells and then to demonstrate that the cells are effectively able to work as intended in treating a disease.

Previous studies showed that treating wild type ES cells with retinoic acid is able to prime neuronal differentiation (Bain et al., 1995). The limit to this study protocol is linked to the side effects retinoic acid carries; retinoic acid is a potent teratogenic agent that causes alterations in the development of the nervous system during embryogenesis in vivo (Soprano and Soprano, 1995; Sucov and Evans, 1995). Hence, it is crucially important to define alternative study protocols. One advantageous alternative strategy to direct cell differentiation includes the introduction of control genes in stem cells development, despite the undesired side effects resulting from clonal variance, dependence on the promoter and ability of some stem cells to suppress the expression of ectopically expressed transgenes (Boehler et al., 2002).

To overcome this problem, it is necessary to identify secreted molecule that can induce and/or inhibit stem cell differentiation toward a selected cell line.

Hence, the objective of the present invention is a method to induce stem cell differentiation into cardiomyocytes, wherein the cells are exposed for a period of time and in efficacious quantities to a protein of the EGF-CFC family or its derivatives, which comprises at least the EGF-CFC domains. Preferably, the EGF and CFC domains derive from the sequence of the Cripto protein, more preferably the EGF and CFC domains derive from the sequence of human Cripto or the EGF and CFC domains derive from the sequence of mouse Cripto.

In an applied form, cell exposure occurs through genetic expression in stem cells via a suitable vector.

Another object of the invention is stem cells induced to differentiate into cardiomyocytes obtained with the described method.

A further object of the invention is a composition for the treatment of heart diseases that comprises stem cells treated according to the described method.

A further object of the invention is the use of the stem cells described for the treatment of heart diseases.

A further object of the invention is a composition for therapeutic use for treating heart disorders that comprises a therapeutically effective quantity of a protein or its derivative, having as a minimum the EGF and CFC domains of a protein of the EGF-CFC family. Preferably, the protein has at least the EGF and CFC domains of the Cripto protein. More preferably, the EGF and CFC domains derive from the human Cripto sequence or from the mouse Cripto sequence.

A further object of the invention is a method to induce stem cell differentiation into neuronal cells, wherein the cells are exposed for a period of time and in efficacious qualities to an inhibitor of the protein Cripto or the engineering of the cells in such a manner that they do not express endogenous functioning Cripto. Preferably, exposure to a Cripto inhibitor occurs in the early phases of stem cell differentiation.

Preferably, the inhibitor of Cripto is an anti-Cripto antibody or its functional fragments; alternatively, it is a peptide specifically selected from a random recombinant peptide library, alternatively it is an antagonist of the Alq4(receptor)-Cripto(co-receptor)-Nodal(ligand) pathway. Preferably, the antagonist is the peptide Cerberus or its functional derivatives.

A further object of the invention is stem cells induced to differentiate into neuronal cell lines obtained by the described method.

A further object of the invention is a composition for the treatment of neuropathologies that comprises the described stem cells.

A further object of the invention is the use of the described stem cells for treating neuropathologies.

A further object of the invention is the use of Cripto or its inhibitors in the preparation of a composition able to direct stem cell differentiation toward the neuronal lineage.

The present invention will now be described using non-restrictive examples in reference to the following figures:

FIG. 1. Schematic representation of the experimental protocol used for ES cell differentiation into cardiomyocytes (adapted from Maltsev et al., 1993).

FIG. 2. Functional dissection of Cripto. Schematic representation of cripto cDNA derivatives. EGF (Epidermal Growth Factor), CFC (Cripto, FrL1, Cripto) (Minchiotti et al., 2001), SP (signal peptide).

(A) Determination of minimal domains required for Cripto activity in cardiomyocyte differentiation. Both wt and deleted cripto mutant derivatives were transfected into Cripto$^{-/-}$ ES cells; empty vector was used as a control. The percentage of EBs with rhythmically contracting areas detectable by light microscopy was scored from days 8 to 12. Data are representative of at least two independent experiments.

(B) Western blot analysis of conditioned media from 293EBNA cells transfected with cripto cDNA deletion derivatives. Cells were cotransfected with Plgf expression vector as an internal control (see Materials and Methods). Lane 1: EGF-CFC; lane 2: EGF long; lane 3: vector. The molecular mass of protein standards is indicated (kDa).

(C) Expression of cardiac specific genes MLC2v and αMHC during in vitro differentiation of either wt or Cripto$^{-/-}$ ES cells. RT-PCR was performed on RNAs extracted from either undifferentiated ES cells or EBs over a 10-day differentiation period (days 2 to 10). HPRT gene expression was analyzed as an internal control.

(D) RNA expression levels of MLC2v and cardiac αMHC genes during in vitro differentiation of Cripto$^{-/-}$ ES cells overexpressing either wild type or cripto deletion mutants. RNA was harvested at days 5, 7 and 10 of the differentiation protocol and subjected to RT-PCR. Empty vector was used as a negative control. HPRT gene expression was analyzed as an internal control. The results are representative of two independent differentiation programs.

Figure 3:
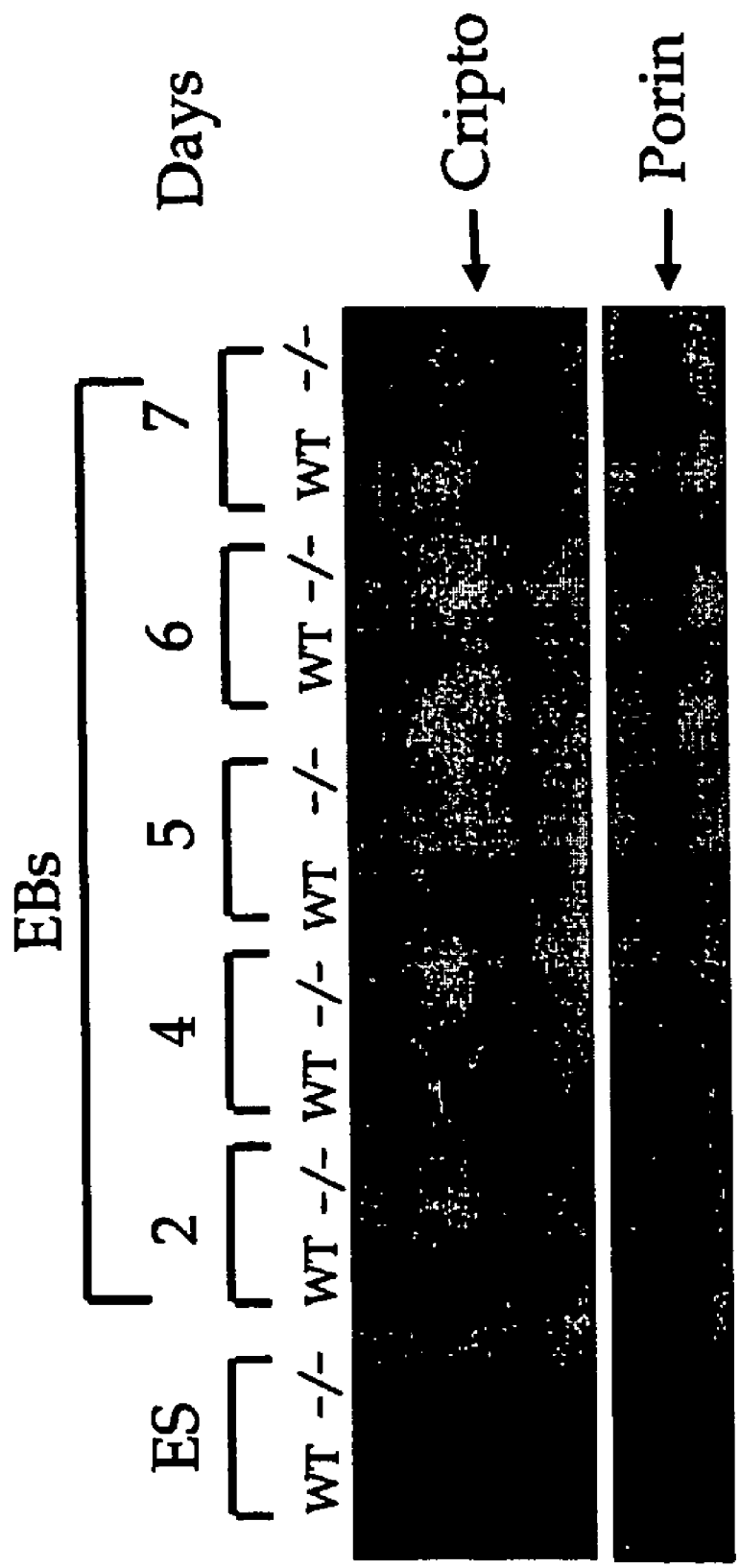

FIG. 3. Cripto expression profile during the in vitro differentiation of ES cells.

Total lysates of either undifferentiated ES cells or EBs at different days of differentiation (from 2 to 7 days), derived from either RI (wt) or DE7 (Cripto$^{-/-}$) ES cells, were collected in lysis buffer and analyzed by Western blot using a polyclonal anti-Cripto antiserum (Minchiotti et al., 2000). Data were normalized to the expression level of Porin.

Figure 4:
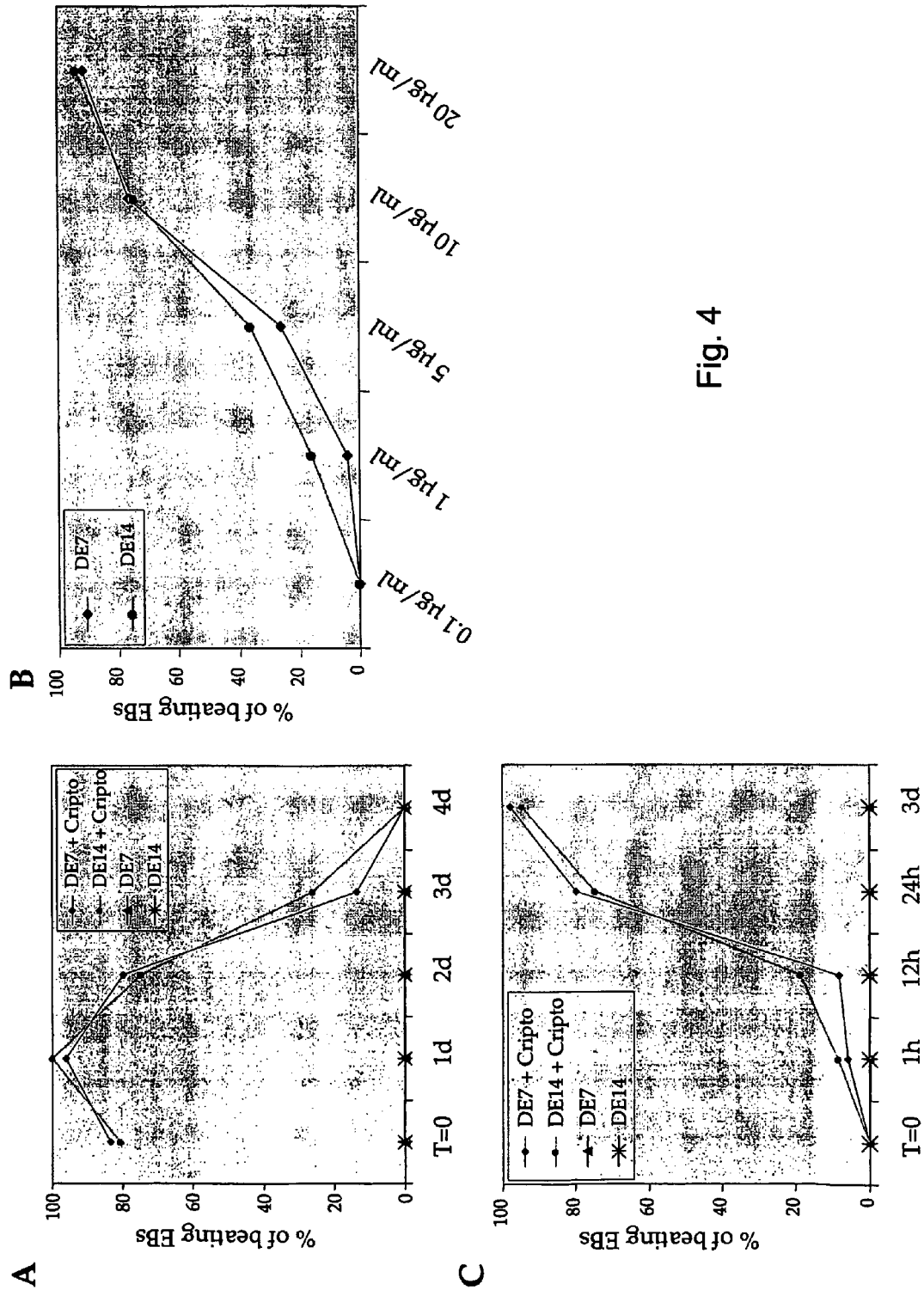

FIG. 4. Dynamics of Cripto signaling during cardiomyocyte differentiation.

a) Definition of the temporal activity of Cripto. Percentage of Cripto$^{-/-}$ EBs containing beating areas after the addition of recombinant Cripto protein. Ten μg/ml of soluble Cripto protein were added to EBs at 24-h intervals starting from time 0 of the in vitro differentiation assay (FIG. 1). The number of EBs containing beating areas was scored from days 8 to 12 of in vitro differentiation.

b) Dose-dependent activity of Cripto protein. Two-day-old Cripto$^{-/-}$ EBs were treated with increasing amounts of recombinant soluble Cripto protein for 24 h, and then cultured for the remaining days. Appearance of beating areas was scored from days 8 to 12 of the in vitro differentiation.

c) Duration of Cripto signaling. Two-day-old Cripto$^{-/-}$ EBs were treated with 10 μg/ml of recombinant soluble Cripto protein for different lengths of time: 1 h, 12 h, 24 h, and 3 days; EBs were then washed to remove the protein and cultured for the remaining days. Cells were examined for cardiac differentiation as described above. In all cases two independent Cripto$^{-/-}$ ES clones (DE7 and DE14) were used. Data are representative of at least two independent experiments.

Figure 5:
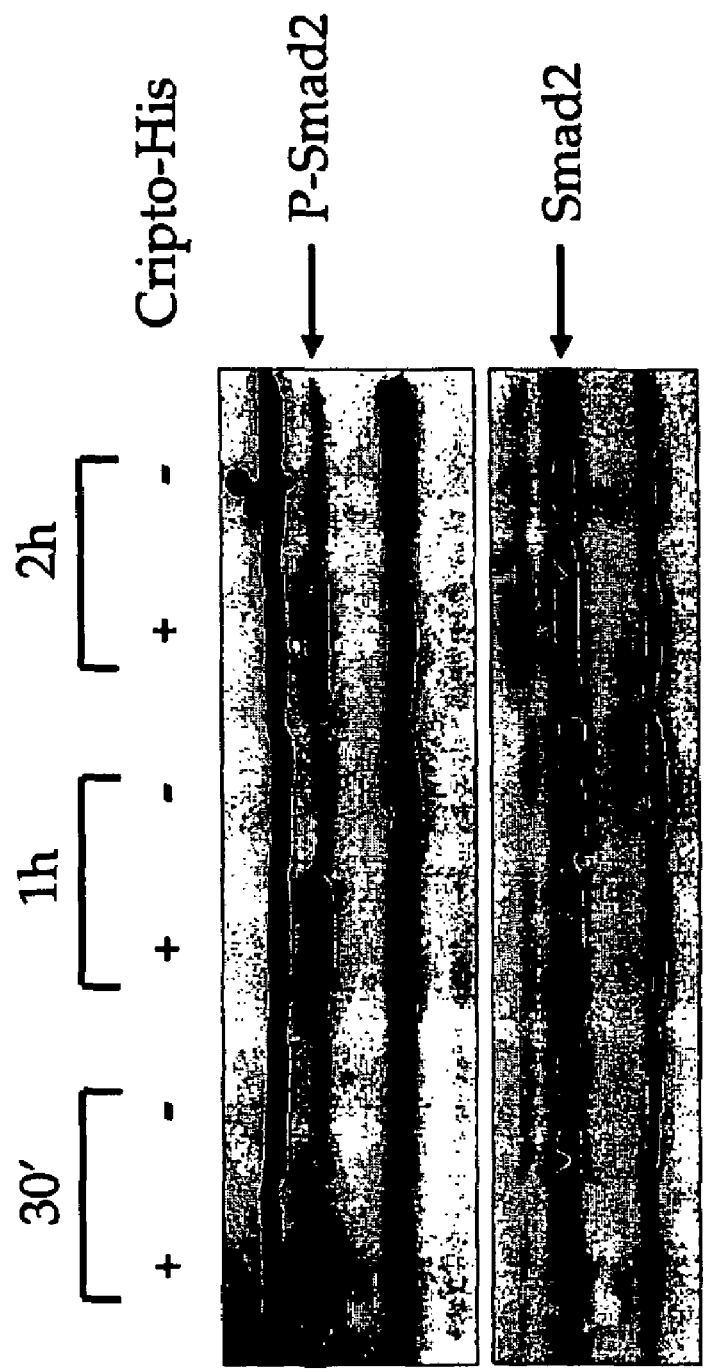

FIG. 5. Activation of Smad2 in Cripto$^{-/-}$ cell aggregates treated with recombinant Cripto protein.

Two-day-old Cripto$^{-/-}$ EBs were serum-starved for 3 h and then treated with 10 μg/ml of recombinant Cripto protein for 30, 60, 120 minutes or left untreated, as indicated. Smad2 activation was detected by Western blot analysis using anti-phospho-Smad2 antibody. Levels of total Smad2 were also compared.

Figure 6:
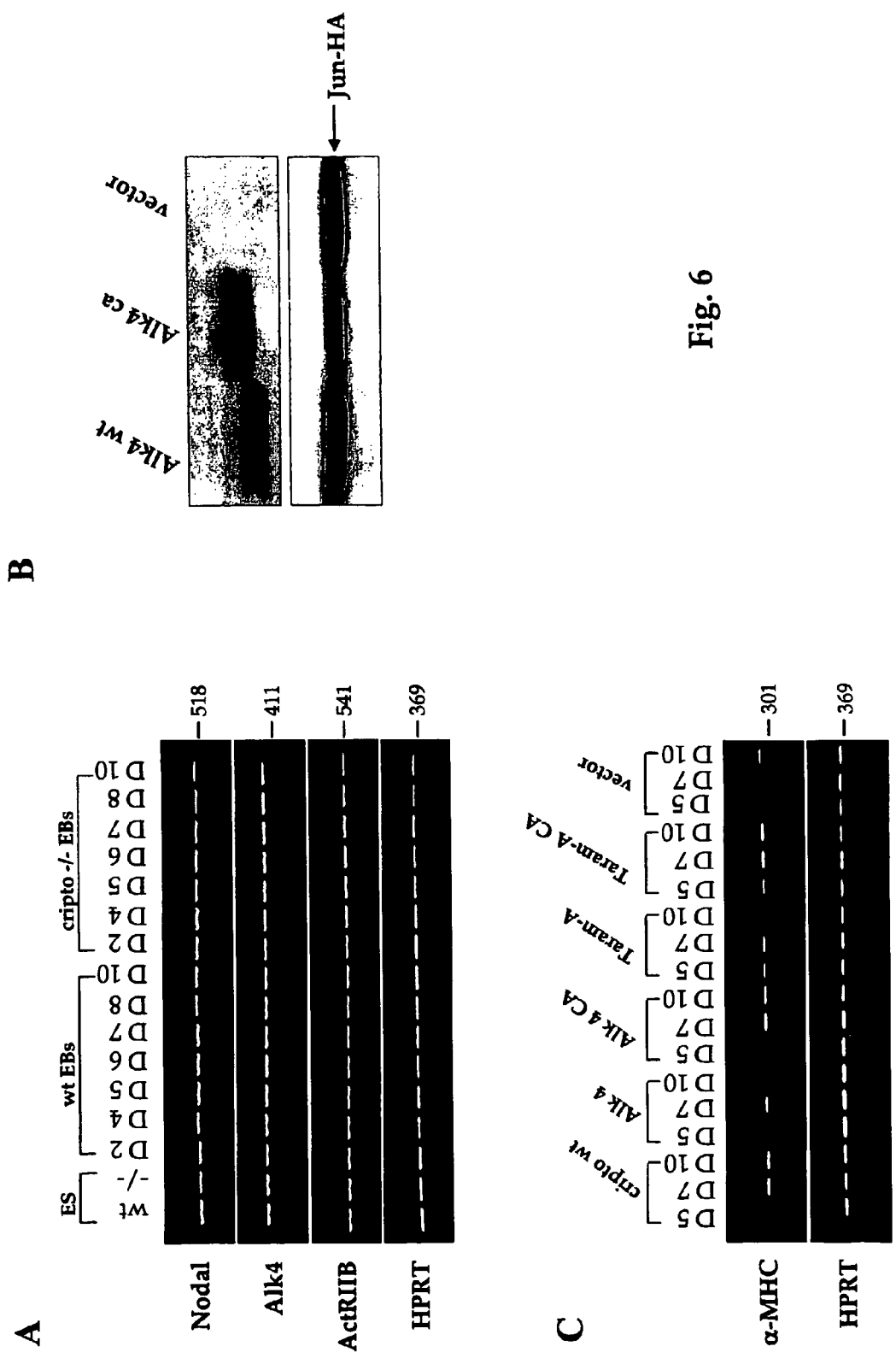

FIG. 6. Expression profile of Nodal, Alk4 and ActRIIB during cardiomyocyte differentiation and their effects on cardiac induction.

(A) RNA expression levels of Nodal, Alk4 and ActRIIB genes during in vitro differentiation of ES cells. RT-PCR analysis was performed on RNAs extracted from either undifferentiated ES or EBs (both wt and Cripto$^{-/-}$) over a 10-day differentiation period (days 2 to 10). HPRT gene was used as an internal control.

(B) Western blot analysis of total lysates from 293EBNA cells transfected with either wild type (wt) or a constitutively activated (ca) form of HA-tagged human Alk4. Cells were cotransfected with Jun-HA expression vector as an internal control. A monoclonal anti-HA antibody was used to detect protein levels.

(C) RNA expression profile of the αMHC gene during differentiation of Cripto$^{-/-}$ ES cells (days 5, 7 and 10) overexpressing wt and activated forms of either Alk4 or Taram-A. HPRT gene was used as an internal control.

Figure 7:
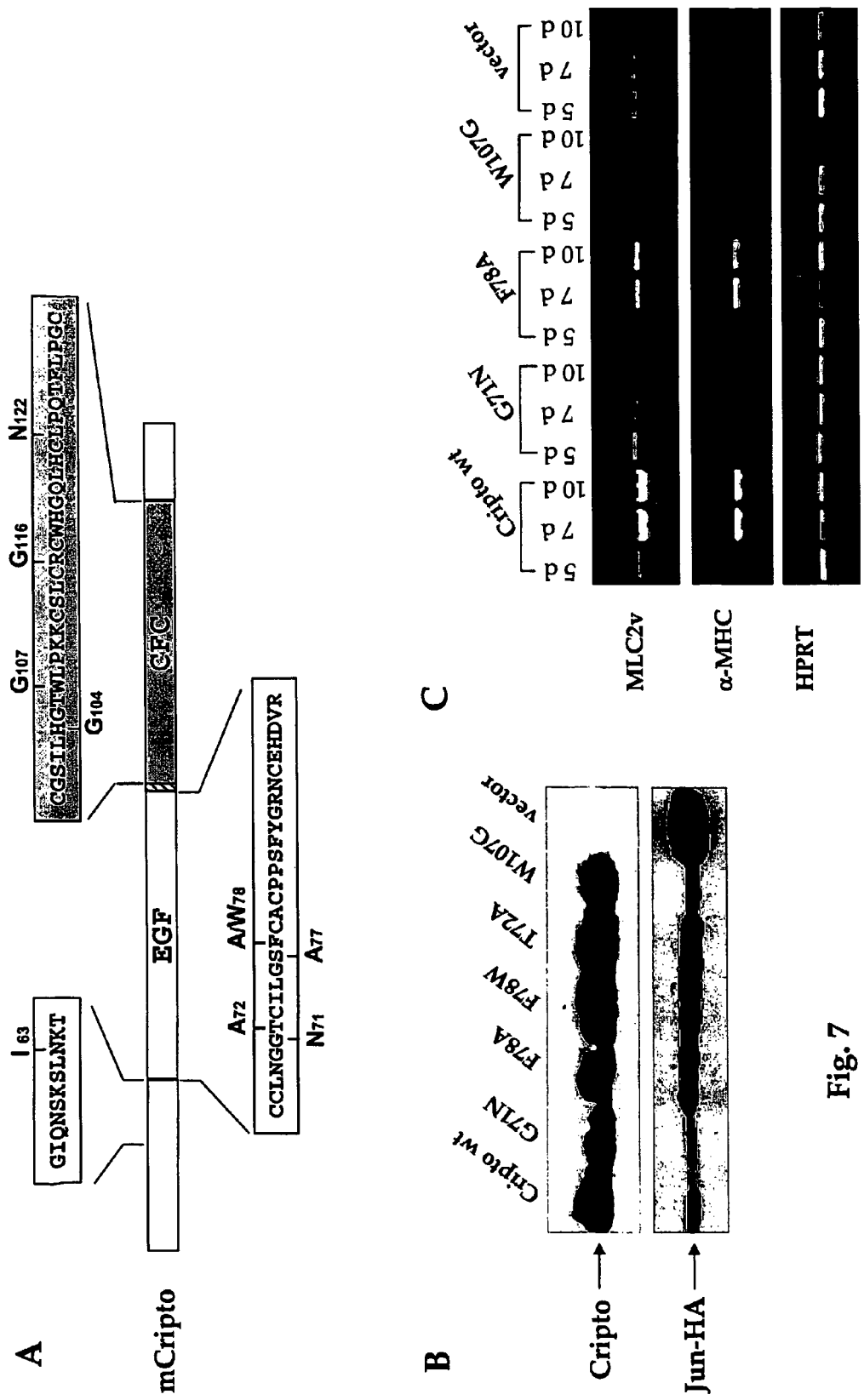

FIG. 7. Identification of Cripto key residues required for cardiac induction and differentiation.

Schematic representation of Cripto wt and mutant derivatives.

(A) Western blot analysis of total lysates from 293EBNA cells transfected with either wt or cripto mutant derivatives. Jun-HA expression vector was cotransfected as an internal control. Either polyclonal anti-Cripto or monoclonal anti-HA antibodies were used to detect protein levels.

(B) RNA expression levels of the cardiac αMHC and MLC2v genes during in vitro differentiation of Cripto$^{-/-}$ ES cells (days 5, 7 and 10) overexpressing either wt or cripto mutant derivatives. Expression level of HPRT gene was analyzed as an internal control.

FIG. 8. Cripto promotes cardiac differentiation and inhibits differentiation to neuronal ES cells.

(A) Cardiac and neuronal differentiation of Cripto$^{-/-}$ EBs as indicated by immunofluorescence assays. Two-day old Cripto$^{-/-}$ EBs were treated (b,d) or not (a,c) with 10 μg/ml of soluble Cripto for 24 h. On day 12 of differentiation, expression of sarcomeric myosin and isotype III β-tubulin were analyzed using anti MF-20 antibodies (red: a,b) and isotype III anti β-tubulin (green: c,d), respectively.

(B) The percentage of Cripto$^{-/-}$ EBs positive to isotype III β-tubulin or MF-20. Ten μg/ml of soluble Cripto were added to the Cripto$^{-/-}$ EBs at 24-h intervals starting from time 0 of in vitro differentiation (cf. diagram in FIG. 1). On day 12 of differentiation, the expression of isotype III β-tubulin and/or sarcomeric myosin were analyzed by immunofluorescence using isotype III β-tubulin antibodies and anti MF-20, respectively.

Materials and Methods

Plasmids and Mutants

The beta-pallino A vector is derived from the pallino expression vector (courtesy of Dr. S. Chiocca) with the following modifications: the CMV promoter is excised as an EcoRI/HindIII DNA fragment and replaced with a SalI/HindIII DNA fragment spanning the chicken α-actin promoter followed by the 3' flanking sequence of the rabbit beta-globin gene (pCXN2 vector; Niwa et al., 1991). Other plasmid vectors may be used as long as the cDNA to be expressed is controlled by transcription promoter sequences and by stabilizer sequencers at 3' active in stem cells, like the β-actin promoter followed by the 3' flanking sequence of β-globin. Restriction sites were blunt-ended using Klenow polymerase. All the cripto mutant derivatives described (both deletions and amino acid substitutions) were obtained by the PCR-based method using the complete cripto cDNA and appropriate oligonucleotides, as previously described (Minchiotti et al., 2001). The cDNA Cripto-His (sequence from nt −5 to nt +468 of the cDNA cripto), here renamed "secreted Cripto", was cloned in the pCDNA3 expression vector (Invitrogen), as described elsewhere (Minchiotti et al., 2001). The cDNAs for cripto EGF long (sequence from nucleotide −5 to nucleotide +288 of cripto cDNA, Dono et al., 1993) and cripto EGF short (sequence from nucleotide −5 to +75 fused to nucleotides +157/+288 of cripto cDNA), wt and activated (ca) Alk4, wt and activated (ca) Taram-A, Cerberus and Cerberus S, were subcloned into beta-pallino A vector for expression in ES cells. When necessary, restriction sites were blunt-ended using Klenow polymerase.

Cell Cultures and ES Differentiation

Human embryonic kidney 293 and 293EBNA cells (ATTC, CRL-1573) and 293T (ATCC,CRL-11268) were cultured in Dulbecco modified Eagle's medium (Celbio) supplemented with 10% fetal bovine serum (Euroclone), 50 U/ml of penicillin and 50 U/ml of streptomycin (GIBCO).

The ES cell lines RI (mouse wild type ES cells, Nagy et al., 1993) and Cripto$^{-/-}$, DE7 and DE14, were used throughout the study. Cripto$^{-/-}$ DE7 and DE14 derive from transfection of two independent Cripto$^{+/-}$ ES clones (Xu et al., 1999). Wild type and Cripto$^{-/-}$ ES cells were maintained in the undifferentiated state by culture on mitomycin C-treated mouse embryonic fibroblast (MEF) feeder layers according to standard protocols. The medium used was high glucose Dulbecco's modified Eagle's medium (Celbio) containing 15% fetal bovine serum (Hyclone), 0.1 mM β-mercaptoethanol (Sigma), 1 mM sodium pyruvate (GIBCO), 1× non essential amminoacids (GIBCO), 2 mM glutamine (GIBCO), 100 U/ml penicillin/streptomycin (GIBCO) and $10^3$ U/ml leukemia inhibitory factor (LIF) (Chemicon). For in vitro differentiation to cardiomyocytes, ES cells were cultivated in embryoid bodies essentially as described (Maltsev et al., 1993; Wobus et al. 1991). Briefly, 400 cells in 20 μl culture medium without LIF (Leukemia Inhibitory Factor used to maintain the ES cells in an undifferentiated state) were placed on the lids of tissue culture dishes filled with PBS and cultivated in hanging drops for 2 days. After further 3 days of culture in bacteriological Petri dishes (FIG. 1) in culture medium without LIF, the 5-day-old EBs were plated separately onto gelatin-coated 48-well plates for morphological analysis, onto 100 mm tissue culture plates for RT-PCR and Western blot. Rhythmic beating of the EBs, which indicates cardiac muscle differentiation, was monitored using phase microscopy (Leica).

Cell Transfection and Protein Purification

Undifferentiated ES cells ($10^7$/ml) were electroporated with linearized DNA (30 μg) at 400 V, 250 □F in 0.9 ml of PBS. Pallino βA derivatives were digested with ScaI; nucleotide mutations were introduced by PCR to eliminate excess ScaI sites, when necessary. The electroporated cells were then plated onto puromycin-resistant STO cells (Smith and Hooper, 1983) in culture medium. Twenty four hours after plating, the medium was replaced with new medium containing 2 μg/ml puromycin and the selection medium was changed every day. At day 7 after electroporation, resistant clones were pooled, expanded and subjected to the differentiation assay. Transfection of 293EBNA cell was performed as previously described (Minchiotti et al., 2000). Transfection efficiency was monitored by cotransfection with a cDNA encoding the Placenta growth factor (Plgf; Maglione et al., 1991).

Recombinant secreted Cripto protein previously named Cripto-His was obtained and purified as previously described (Minchiotti et al., 2001). In brief, the protein was purified from the medium conditioned by a stably transfected clone of 293 cells obtained with the cripto-His pCDNA3 vector (Minchiotti, et al., 2001) using the Qiaexpress protein purification system (Quiagen). The purified protein was dialyzed against 50 mM sodium phosphate buffer, pH 8. The recombinant Cripto-Fc protein was purified from the medium conditioned by 293T cells transfected with the CriptoFc/pIg vector according to the manufacturer's instructions (R&D).

Western Blotting and Smad2 Induction

Undifferentiated (wt or Cripto$^{-/-}$) ES cells or EBs derived from either wt (RI) or Cripto$^{-/-}$ (DE7) ES cell lines at different stages during in vitro differentiation were lysed in a buffer containing: 10 mM Tris/Cl pH 8, 140 mM NaCl, 2 mM EDTA pH 8, 1% NP-40 and analyzed by Western blot as previously described (Minchiotti et al., 2000). The anti-HA (12CA5) monoclonal antibody (ROCHE) and anti-Porin 31HL antibody (Calbiochem, cat. #529538) were used according to manufacturer's instructions.

Two-day-old Cripto$^{-/-}$ EBs were starved for 3 h in medium without LIF and in low serum (1%), after which Cripto-His protein was added directly to the same medium. At the indicated time, EBs were dissolved in Laemmli lysis buffer (Laemmli, 1970) and analyzed by Western blot using the Trans-Blot Semi-dry System (BIO-RAD), following manufacturer's instructions. Rabbit polyclonal anti-Smad2/3, anti-phospho-Smad2 (Ser465/467) (Upstate Biotechnology) and anti-phospho-ERK (Santa Cruz Biotechnology, Inc.) antibodies were used following the manufacturer's instructions.

RNA Preparation and RT-PCR

Total RNA from either undifferentiated ES cells or EBs from different stages of in vitro differentiation was extracted with TRIzol kit (Life Technologies Inc.) according to manufacturer's instructions and reverse transcribed to cDNA with SuperScript II reverse transcriptase (Life Technologies Inc.) and random hexamers (as primers). cDNA samples synthesized from 100 ng of total RNA were subjected to PCR amplification with specific primers. The primers and the PCR conditions used were as follows:

```
    Nodal:
    F,          5'TTCCTTCTCAGGTCACGTTTGC3';
    R,          5'GGTGGGGTTGGTATCGTTTCA3,
``` annealing temperature: 58° C., cycles: 35, 518 bp fragment;

```
    ALK-4:
    F,          5'AAGGATCCAGGCTCTGCTGTGTGGC3';
    R,          5'ACGGATCCATGTCCAACCTCTGGCGG3',
``` annealing temperature: 60° C., cycles: 30, 411 bp fragment;

```
    ActRIIB:
    F,          5'ATGTGCCGTGGTGTCGTGGT3'
    R,          5'GACCTCCTGATCAGGGATAC,
``` annealing temperature: 58° C., cycles: 30, 541 bp fragment;

```
    MLC2v:
    F,          5'GCCAAGAAGCGGATAGAAGGCGGG3';
    R,          5'CTGTGGTTCAGGGCTCAGTCCTTC3';
``` annealing temperature: 70° C., cycles: 33, 490 bp fragment;

```
    cardiac αMHC:
    F,          5'GGAAGAGTGAGCGGCGCATCAAGG3'
    R,          5'CTGCTGGAGAGGTTATTCCTCG3',
``` annealing temperature: 65° C., cycles: 30, 301 bp fragment;

```
    HPRT:
    F,          5'CCTGCTGGATTACATTAAAGCACTG3'
    R,          5'CCTGAAGTACTCATTATAGTCAAGG3',
``` annealing temperature: 58° C., cycles: 25, 369 bp fragment; used as control.

Cripto Mutant Derivatives

All cripto mutants (both deletion and substitution) were obtained using a PCR-based method with complete Cripto cDNA as described (Minchiotti et al., 2001); in all cases the amplified fragments were sequenced in both directions with the dideoxy nucleotide procedure.

A. Deletion Mutants cDNA Cripto-His (sequence from nt −5 to nt +468 of cripto cDNA) was cloned in the pCDNA3 expression vector (Invitrogen) or into β pallino. The cDNA Cripto-FC (sequence from nt −5 to nt +468 of cripto cDNA) was produced using the pIg-tail expression system (N. MBK-006-5, R&D). Both the cDNA have been previously described elsewhere (Minchiotti et al., Development, 2001: 4501-4510).

B. Point Mutants

The cDNA cripto derivatives were obtained using the following nucleotides:

```
  1. Asn63-Ile
     5'-GTAAGTCGCTTATTAAAACTTGCTGTC-3'
     5'-GACAGCAAGTTTTAATAAGCGACTTAC-3'

2. Gly71-Asn
     5'-CTTGCTGTCTGAATGGAAACACTTGCATCCTGGGGTCC-3'
     5'-GGACCCCAGGATGCAAGTGTTTCCATTCAGACAGCAAG-3'

3. Thr72-Ala
     5'-GAATGGAGGGGCTTGCATGCTGG-3'
     5'-CCAGGATGCAAGCCCCTCCATTC-3'

4. Ser77-Ala
     5'-CTTGCATCCTGGGGGCCTTCTGTGCGTGC-3'
     5'-GCAGGCACAGAAGGCCCCCAGGATGCAAG-3'

5. Pbe78-Ala
     5'-GCATCCTGGGGTCCGCCTGTGCCTGCCCTCC-3'
     5'-GCATCCTGGGGTCCGCCTGTGCCTGCCCTCC-3'

6. Phe78-Trp
     5'-GCATCCTGGGGTCCTGGTGTGCCTGCCCTCC-3'
     5'-GGAGGGCAGGCACACCAGGACCCCAGGATGC-3'

7. His104-Ala
     5'-GTGGGTCTATCCTCGCTGGCACCTGGCTGCCC-3'
     5'-GGGCAGCCAGGTGCCAGCGAGGATAGACCCAC-3'

8. Trp107-Gly
     5'-CATGGCACCGGGCTGCCCAAG-3'
     5'-CTTGGGGAGCCCGGTGCCATG-3'

9. Arg116-Ala
     5'-GTGTTCCCTGTGCGCATGCTGGCACGGCCAG-3'
     5'-GTGGCCGTGCCAGCATGCGCACAGGGAACAC-3'

10. Leu122-Asn
     5'-GCTGGCACGGCCAGAACCACTGTCTTCCTCAG-3'
     5'-CTGAGGAAGACAGTGGTTCTGGCCGTGCCAGC-3'
```

The cDNAs for Alk4 WT and activated (CA), Taram-A WT and activated (CA), activated smad2 (smad2CA) and activated Ras (RasCA) were subcloned into pallino βA for expression in ES cells. When necessary, the restriction sites were blunt-ended by Klenow polymerase.

The following protein sequences were obtained:

```
mCripto
MGYFSSSVVLLVAISSAFEFGPVAGRDLAIRDNSIWDQKEPAVRDRSFQF

VPSVGIQNSKSLNKTCCLNGGTCILGSFCACPPSFYGRNCEHDVRKEHCG

SILHGTWLPKKCSLCRCWHGQLHCLPQTFLPGCDGHVMDQDLKASRTPCQ

TPSVTTTFMLAGACLFLDMKV
```

Nucleotides from −5 to +516 (Dono et al., 1993)

Amino acids 1-171 (Dono et al., 1993)

```
Secreted (mCripto)
MGYFSSSVVLLVAISSAFEFGPVAGRDLAIRDNSIWDQKEPAVRDRSFQF

VPSVGIQNSKSLNKTCCLNGGTCILGSFCACPPSFYGRNCEHDVRKEHCG

SILHGTWLPKKCSLCRCWHGQLHCLPQTFLPGCDGHVMDQDLKASRTPCQ

TPSVTT
```

Nucleotides from −5 to +468 of the Cripto sequence (Dono et al., 1993)

Amino acids 1-156 of the Cripto sequence (Dono et al., 1993)

Secreted His-tagged (mCripto His)
MGYFSSSVVLLVAISSAFEFGPVAGRDLAIRDNSIWDQKEPAVRDRSFQF

VPSVGIQNSKSLNKTCCLNGGTCILGSFCACPPSFYGRNCEHDVRKEHCG

SILHGTWLPKKCSLCRCWHGQLHCLPQTFLPGCDGHVMDQDLKASRTPCQ

TPSVTT<u>TNSGHHHHHH</u>

Nucleotides from −5 to +468 of the Cripto sequence (Dono et al., 1993)
Amino acids 1-156 of the Cripto sequence (Dono et al., 1993)
Amino acids 157-166 His-tag EGF-CFC (mCripto)
MGYFSSSVVLLVAISSAFEFGPVAGSVGIQNSKSLNKTCCLNGGTCILGS

FCACPPSFYGRNCEHDVRKEHCGSILHGTWLPKKCSLCRCWHGQLHCLPQ

TFLPGCDGHVMDQDLKASRTPCQTPSVTT

Nucleotides from −5 to +75 fused to +157 at +468 of the mouse Cripto sequence (Dono et al., 1993)
Amino acids 1-25 fused to 53-156

EGF-CFC His-tagged (mCripto)
MGYFSSSVVLLVAISSAFEFGPVAGSVGIQNSKSLNKTCCLNGGTCILGS

FCACPPSFYGRNCEHDVRKEHCGSILHGTWLPKKCSLCRCWHGQLHCLPQ

TFLPGCDGHVMDQDLKASRTPCQTPSVTT<u>TNSGHHHHHH</u>

Nucleotides from −5 to +75 fused at +157 at +468 of the mouse Cripto sequence (Dono et al., 1993)
Amino acids 1-25 fused at 53-156
Amino acids 157-166 His-tag EGF short (mCripto)
MGYFSSSVVLLVAISSAFEFGPVAGSVGIQNSKSLNKTCCLNGGTCILGS

FCACPPSFYGRNCEHDVRK

Nucleotides from −5 to +75 fused at +157 at +288 (Dono et al., 1993)
Amino acids 1-25 fused at 53-96

EGF long (mCripto)
MGYFSSSVVLLVAISSAFEFGPVAGRDLAIRDNSIWDQKEPAVRDRSFQF

VPSVGIQNSKSLNKTCCLNGGTCILGSFCACPPSFYGRNCEHDVRK

Nucleotides from −5 to +288 of the mouse Cripto sequence (Dono et al., 1993)
Amino acids 1-96 (Dono et al., 1993)

hCripto
MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTTTFMLVGACLFLDMKV

Nucleotides from 244 to 814 of the human Cripto sequence (Ciccodicola et al. 1989).
Amino acids 1-188 (Dono et al., 1993)

hCripto secreted
MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTT

Nucleotides from 244 to 766 of the human Cripto sequence (Ciccodicola et al., 1989).
Amino acids 1-173 (Dono et al., 1993)

hCripto secreted his-tagged
MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTT<u>TNSGHHHHHH</u>

Nucleotides from 244 to 766 of the human Cripto sequence
Amino acids 1-173 (Dono et al., 1993)
Amino acids 174-183 His tag Immunofluorescence on EB The EB were grown in adhesion. On day 12 of differentiation, they were fixed for 30 minutes at room temperature in a solution of 4% paraformaldehyde for treatment with isotype III β-tubulin antibody (Sigma) or on ice in a solution of methanol:acetone at a ratio of 7:3 for treatment with anti-sarcomeric myosin MF-20 (Developmental Studies Hybridoma Bank, University of Iowa, Dept. of Biological Sciences, Iowa City, USA). After 3 washings with phosphate buffer (PBS, GIBCO cat no. 20012-019), the EB were treated with 0.1% Triton X-100 (Sigma), 10% pre-immune goat serum (DAKO, code no. X0907) in PBS and then incubated with their respective primary antibodies in a 10% solution of pre-immune goat serum in PBS for 2 h at room temperature. The primary antibody dilutions were: isotype III anti β-tubulin (1:400), MF-20 (1:50). The EBs were then washed with PBS and incubated at room temperature for 30 minutes in a 10% solution of pre-immune goat serum in PBS in the presence of the following secondary antibodies: mouse anti-antibody produced in goat and conjugated with rodamine (Jackson Laboratories, primary antibody MF-20) and mouse anti-antibody produced in goat and conjugated with fluorescein (Jackson Laboratories, primary antibody isotype III anti β-tubulin). The EBs were then thoroughly washed in PBS and counterstained with DAPI (4',6-diamidino-2-phenylindole hydrochloride, SIGMA) to visualize the nuclei. Lastly, the EBs were mounted using a Vecta Shield (Vector Laboratories, Burlingame, Calif., USA) for epifluorescent light microscopy. The images were acquired using an Axiocam ARC system (Zeiss).

Results

Secreted Cripto Retains its Ability to Rescue Cardiomyocyte Differentiation

Previous data on cultured ES cells lacking cripto have revealed an essential role of cripto for contractile cardiomyocyte formation. Cripto$^{-/-}$ ES cells selectively lose the ability to form beating cardiomyocytes, a process that can be rescued by expression of Cripto (Xu et al., 1998). However, it is highly advantageous to determine whether a secreted form of Cripto can restore cardiomyocyte differentiation in Cripto$^{-/-}$ ES cells. To this end, we overexpressed a secreted derivative of Cripto lacking the hydrophobic C-terminus region required for membrane anchorage (Minchiotti et al., 2000) in Cripto$^{-/-}$ ES cells and compared its activity to that of wt Cripto. A pooled population of cells selected for resistance to puromycin was examined for the number of EBs containing beating areas from days 8 to 12 of in vitro differentiation (FIGS. 1, 2A). Spontaneous rhythmic contractile myocytes were observed in Cripto$^{-/-}$ ES cells expressing either the membrane-anchored or the secreted Cripto protein (FIG. 2B). Moreover, similar results were obtained by expressing a secreted Cripto protein which lacks the N-terminus region (EGF-CFC; FIGS. 2A and 2B), thus indicating not only that membrane anchorage is dispensable for activity, but also that the EGF-CFC domain alone is sufficient for Cripto activity in cardiogenic induction. It was then necessary to define whether the Cripto EGF-like domain alone was able to induce cardiogenesis similar to the EGF-CFC peptide. Two cripto cDNA deletion derivatives encoding either the EGF-like domain retaining the N-terminus region (EGF long) or just the EGF domain (EGF short, FIG. 2A) were generated. No beating areas cells were observed in EBs derived from Cripto$^{-/-}$ ES cells expressing either the EGF long or the EGF short peptide (FIG. 2B), thus indicating that at least the CFC domain of Cripto is essential for cardiogenic induction. Western blot analysis showed that the EGF long peptide was produced and secreted as efficiently as EGF-CFC (FIG. 2C), thus demonstrating that its inability to rescue the mutant phenotype is not due to a difference at the protein expression level. Similar results were obtained with the EGF short construct. To support the morphological data observed, we examined the expression of the cardiac-specific myosin heavy chain ($\alpha$MHC) and myosin light chain 2v (MLC2v), two major contractile proteins of cardiomyocytes. As expected, expression of the ☐MHC and MLC2v genes was induced in wt ES cells but not in Cripto$^{-/-}$ cells from day 7 of in vitro differentiation (FIG. 2D). The expression pattern of ☐MHC and MLC2v genes in wt ES cells was reproduced in Cripto$^{-/-}$ cells expressing both wt Cripto and the secreted derivative, but not in cells expressing the EGF long or the EGF short peptides (FIG. 2E).

Timing and Duration of Cripto Activity in Cardiomyocyte Differentiation

The timing of Cripto expression during ES cell differentiation was examined. Western blot analysis performed with anti-Cripto antibodies on lysates from both wt and Cripto$^{-/-}$ ES cells revealed that Cripto was detectable as early as day 0 and peaked in expression by day 4 in wt EBs (FIG. 3). The transient nature of Cripto accumulation suggests that its activity might be required at a defined step in cardiomyocyte differentiation. Since transfection assays do not adequately investigate the window of Cripto action, a recombinant soluble Cripto protein was used in which the hydrophobic C-terminus was replaced with a 6×His epitope (Cripto-His; Minchiotti et al., 2001). Based on the observation that secreted Cripto protein is able to promote cardiogenesis when expressed in the Cripto$^{-/-}$ ES cells (FIG. 2B), experiments were performed where Cripto signaling was reconstituted by adding recombinant secreted Cripto protein directly to the cells (FIG. 4). The addition of Cripto during the 0-2 day interval effectively restores the differentiation ability of Cripto$^{-/-}$ ES cells. Addition at later time points results in dramatically reduced cardiomyocyte differentiation (FIG. 4A). Comparable results were obtained with two independent Cripto$^{-/-}$ ES clones (DE7 and DE14; Xu et al., 1998), thus excluding any phenotype difference due to clonal variation (FIG. 4A). Taken together, these data indicate that stimulation in trans with soluble Cripto protein is fully efficient in promoting cardiomyocyte induction and differentiation and, more interestingly, the data define exactly when Cripto activity is required to promote specification of the cardiac lineage. Furthermore, to define optimal concentrations of Cripto required to promote cardiogenesis, increasing amounts of purified recombinant Cripto protein were added directly to the culture medium of 2-day-old Cripto$^{-/-}$ EBs from either DE7 or DE14 cell lines for 24 h (FIG. 4B). Increasing amounts of recombinant Cripto enhance differentiation efficiency (FIG. 4B), thus indicating that Cripto-mediated cardiogenic induction is dose-dependent.

We then wanted to define whether the duration of Cripto signaling was crucial for its biological response. Two-day-old EBs from DE7 or DE14 Cripto$^{-/-}$ ES cells were treated with 10 µg/ml of recombinant Cripto for various lengths of time, washed to remove unbound Cripto, and then cultured for the remaining days. An effective Cripto response requires a minimum induction of 24 h, while shorter inductions show markedly reduced activity (FIG. 4C). Taken together, our data demonstrate that the amount, timing and duration of Cripto signaling are all crucial factors for achieving cardiogenic induction and differentiation.

Cripto Activates a Smad2 Pathway Associated with Cardiomyocyte Differentiation

Findings in mice, Xenopus and Zebrafish point to a strong functional link between the EGF-CFC proteins and Transforming Growth Factor alpha (TGF$\alpha$)-ligand (Adamson et al., 2002; Shen and Schier, 2000). Accordingly, recent studies have shown that Cripto can associate with type I receptor ActRIIB (Alk4) and can form a complex together with Nodal and type II receptor ActRIIB (Reissman et al., 2001; Yeo and Whitman, 2001, Bianco et al., 2002; Yan et al., 2002). Activation of a Smad protein by phosphorylation is a universal signal transduction event following activation of Alk receptors. To determine whether Cripto activates the Smad2 pathway during cardiomyocyte induction and differentiation, 2-day-old Cripto$^{-/-}$ EBs were starved in low serum for 3 h and then stimulated with recombinant soluble Cripto protein for 30, 60 or 120 minutes. Western blot analysis revealed that phosphorylation of Smad2 significantly increases after treatment with recombinant Cripto. Smad2 phosphorylation was detectable already after 30 minutes of treatment and persisted at comparable levels even after prolonged exposure to Cripto protein. An anti Smad-2-3 antibody applied to the same blot was used to normalize for total amount of protein (FIG. 5). In vitro studies on mammalian cell lines have suggested that Cripto is involved in the Ras/Raf/MEK/MAPK pathway (Salomon et al., 1999). The search for activation of the MAP kinase ERK by using an anti-phospho-ERK antibody revealed that recombinant Cripto was unable to activate MAP kinase, thus indicating that the Smad2 pathway is selectively activated during cardiomyocyte induction and differentiation induced by Cripto.

Since no data are available on the expression profile of all components of the Alk4/ActRIIB/Nodal complex during the differentiation of ES cells, we first measured by RT-PCR the expression of Nodal, Alk4 and ActRIIB in EBs derived from both wt and Cripto$^{-/-}$ ES cells. Nodal, Alk4 and ActRIIB were expressed in all analyzed stages (FIG. 6A). If Cripto signaling in cardiomyocyte differentiation acts via the Alk4 receptor, overexpression of a constitutively active type I receptor would be expected to compensate for the lack of Cripto signaling in promoting cardiomyocyte differentiation. To this end, we overexpressed in Cripto$^{-/-}$ ES cells the wild type (wt) or the activated form (ca) of both human HA-tagged Alk4 and its Zebrafish counterpart Taram-A (Renucci et al., 1996). Type I receptor serine/threonine kinases can be activated in a ligand- and type II receptor-independent manner by replacing an acidic residue with a specific threonine within the juxtamembrane region of the intracellular domain, a segment known to be involved in kinase regulation (Wieser et al., 1995). Overexpression of either Alk4 ca or Taram-A ca partially restores the ability of Cripto$^{-/-}$ ES cells to differentiate into cardiomyocytes (Table 1). In contrast, overexpression of the wt receptors, both Taram-A and Alk4, have no significant activity despite their similar expression levels (FIG. 6B). In accordance with the morphological data, expression of the alphaMHC gene was only detected in Cripto$^{-/-}$ ES cells expressing the activated form of the receptors (FIG. 6C).

Recent data in Zebrafish have shown that intracellular activation of the Nodal pathway, induced by expression of an activated form of the Taram-A receptor, is sufficient to commit cells to an endodermal fate and behavior (David and Rosa, 2001). To exclude the possibility that activated Alk4 may interfere in this way with cardiomyocyte specification, recombinant Cripto was added to Alk4 ca expressing cells. Cripto treatment fully restores differentiation, indicating that the activated receptor has no inherent adverse effect on cardiomyocyte specification (Table 2).

Analysis of Cripto Mutants Identifies Key Residues in Both the EGF and the CFC domains As demonstrated, the EGF-CFC domain is sufficient to promote cardiogenic induction when overexpressed in Cripto$^{-/-}$ ES cells, whereas the EGF domain alone is unable to rescue such biological activity. To determine the contribution of the EGF and the CFC domains, single amino acid substitutions were introduced in the cripto cDNA (FIG. 7A) and the activity of the corresponding mutant proteins was compared with the wt in the cardiomyocyte assay. While each mutant was expressed at levels comparable with wt Cripto (FIG. 7B), three of them were completely inactive or showed a strongly reduced activity (Table 3). Similar results were obtained with two independent Cripto$^{-/-}$ ES clones (Table 3). To support the observed morphological data, the expression of the αMHC and the MLC2v genes was examined by RT-PCR on total RNA prepared from EBs derived from Cripto$^{-/-}$ ES cells overexpressing Cripto mutant derivatives (FIG. 7C). Expression of αMHC and MLC2v genes was either absent or reduced in cells overexpressing G71N, F78A or W107G cripto mutants, whereas it was restored in Cripto$^{-/-}$ cells transfected with wt cripto. Taken together, these data show that critical amino acid residues are located both in the EGF and in the CFC domains, thus indicating that both EGF and CFC domains are required for Cripto activity in cardiogenic induction.

Recent reports have shown that Cripto is modified by the addition of sugar residues. N-linked glycosylation was shown to affect Cripto biological activity in the Zebrafish assay (Minchiotti et al., 2001). More recently, an O-linked fucosylation of Cripto has been reported to be required for Cripto signaling activity in cotransfection assay in mammalian cells (Schiffer et al., 2001; Yan et al., 2002). To assess whether post-translational modifications are required for Cripto activity in cardiogenic induction, two alanine substitutions were generated, corresponding to the N-glycosylation site (N631) and the O-linked fucosylation site (T72A). The activities of the corresponding mutant proteins were tested in the differentiation assay and compared with wt Cripto. Based on the percentage of EBs containing beating areas, both mutant proteins have a similar ability to promote cardiomyocyte differentiation in comparison with wt Cripto (Table 3), thus suggesting that the addition of sugar residues is not strictly required for Cripto activity in ES cells.

TABLE 1

Percentage of beating EBs from Cripto$^{-/-}$ ES cells transfected with either the wild type or the constitutively activated form of human Alk4 or Zebrafish Taram-A receptors.

| Cells | Construct | EBs scored | % of beating EB |
|---|---|---|---|
| DE7 | None | 70 | 0 |
| DE7 | Cripto wt | 50 | 96.6 |
| DE7 | Alk4 wt | 76 | 0 |
| DE7 | Alk4 ca | 50 | 16.0 |
| DE7 | Taram-A wt | 55 | 0 |
| DE7 | Taram-A ca | 64 | 45.0 |
| DE7 | Empty vector | 56 | 0 |
| DE14 | None | 80 | 0 |
| DE14 | Cripto wt | 54 | 94.4 |
| DE14 | Taram-A wt | 50 | 1.9 |
| DE14 | Taram-A ca | 51 | 62.2 |
| DE14 | Empty vector | 60 | 0 |

The data are representative of at least two independent experiments. DE7 and DE14 are two independent Cripto$^{-/-}$ clones (see Materials and Methods).

TABLE 2

Percentage of beating EBs from transfected Cripto$^{-/-}$ ES cells.

| Construct | Protein | EBs scored | % of beating EB |
|---|---|---|---|
| Alk4 ca | None | 50 | 16.0 |
| Alk4 ca | Cripto* | 87 | 87.3 |
| Empty vector | None | 49 | 0 |
| Empty vector | Cripto* | 60 | 96.6 |

*Two-day-old EBs treated with 10 μg/ml of recombinant Cripto for 3 days.

TABLE 3

Percentage of beating EBs from Cripto$^{-/-}$ ES cells transfected with Cripto wt or Cripto mutant derivatives.

| Cells | Construct | EBs scored | % of beating EBs |
|---|---|---|---|
| DE7 | None | 97 | 0 |
| DE7 | Cripto wt | 56 | 98.2 |
| DE7 | N63I | 54 | 91.5 |
| DE7 | G71N | 54 | 0 |
| DE7 | T72A | 62 | 90.3 |
| DE7 | S77A | 60 | 95.0 |
| DE7 | F78A | 47 | 42.5 |
| DE7 | F78W | 60 | 95.0 |
| DE7 | H104A | 56 | 89.3 |
| DE7 | W107G | 57 | 7.6 |
| DE7 | R116G | 49 | 80.0 |
| DE7 | L122N | 103 | 92.0 |
| DE7 | Empty vector | 65 | 0 |
| DE14 | None | 85 | 0 |
| DE14 | Cripto wt | 54 | 94.4 |
| DE14 | G71N | 49 | 0 |
| DE14 | F78A | 45 | 66.0 |
| DE14 | W107G | 57 | 30.5 |
| DE14 | Empty vector | 71 | 0 |

The data are representative of at least two independent experiments. DE7 and DE14 are two independent Cripto$^{-/-}$ clones (see Materials and Methods).

Cripto$^{-/-}$ ES Cells Differentiate into Neurons without Inductive Stimulation When plated on an adhesive substrate, the Cripto$^{-/-}$ EBs showed the presence of a dense cell network with a morphology like that of neurons. This characteristic morphology is never found in wild type EBs or in Cripto$^{-/-}$ EBs where Cripto signaling was rescued by adding recombinant protein or by transfection with a Cripto expression vector. To confirm that the cells were effectively neurons, immunofluorescence assays were performed on Cripto$^{-/-}$ EBs treated or untreated with recombinant secreted Cripto using antibodies that recognize a neuron-specific form of the protein βIII-tubulin. This antibody identifies cell groups positive to EBs derived from Cripto$^{-/-}$ ES cells not treated with Cripto protein, thus demonstrating that they are effectively neurons (FIG. 8A). Moreover, 70% of Cripto$^{-/-}$ EBs scored showed cells positive to the isotype III anti-β-tubulin antibody, indicating the presence of an elevated percentage of neurons. Cells positive to the isotype III anti-β-tubulin antibody are completely absent in Cripto$^{-/-}$ EBs treated with Cripto protein which, in contrast, showed an ample area of cells positive to the MF-20 antibody that recognizes sarcomeric myosin and was utilized to visualize the cardiomyocytes (FIG. 8). These data indicate that the absence of Cripto in ES cells causes the spontaneous differentiation of neurons without inductive stimuli.

To modulate Cripto signaling, the protein was added at various time points during differentiation of EBs derived from Cripto$^{-/-}$ ES cells. The addition of Cripto during the 0-2-day window of differentiation again promoted cardiomyocyte differentiation, while dramatically reducing the number of EBs displaying neurons, indicating that the rescue of Cripto signaling inhibits the ability of EBs to spontaneously differentiate into neurons. In contrast, the addition of Cripto during a different time window (3-6 days) did not rescue the cardiac phenotype of Cripto$^{-/-}$ ES cells nor did it alter the ability of the cells to spontaneously differentiate into neurons, as indicated by the high percentage of EBs demonstrating the presence of neurons and the absence of cardiomyocytes. These results indicate that Cripto signaling in a narrow, very early time window (0-2 days) of differentiation inhibits neural differentiation of ES cells and primes them for cardiac differentiation.

Nodal Antagonists Inhibit Cripto Activity in Cardiomyogenesis

To have direct proof that the Nodal signal is effectively needed for Cripto-regulated induction of ES cells toward the cardiac lineage, we investigated whether Nodal inhibition could interfere with the ability of Cripto to prime cardiomyogenesis. Cripto$^{-/-}$ ES cells were transfected with expression vectors for Cerberus, a known Nodal antagonist protein (Piccolo et al., 1999), before treating EBs derived from recombinant Cripto. This multifunctional antagonist inhibits Nodal similarly to BMP and Wnt signaling. A truncated form of Cerberus, Cerberus-Short (CerS), is a specific antagonist only against Nodal (Piccolo et al., 1999). The expression of Cerberus and Cerberus-S significantly inhibits Cripto activity (Table 4). These results show that Cerberus and Cerberus-S can act as effective antagonists against Cripto signaling in ES cell differentiation, confirming the functional role of the Nodal pathway in Cripto-mediated induction of the cardiac lineage.

TABLE 4

Percentage of beating EBs from Cripto$^{-/-}$ ES cells transfected with Nodal antagonists.

| Construct | Protein | EBs scored | % of beating EB |
|---|---|---|---|
| Empty vector | None | 40 | 0 |
| Empty vector | Cripto$^a$ | 58 | 85 |
| Cerberus | None | 34 | 0 |
| Cerberus | Cripto$^a$ | 49 | 10.3 |
| Cerberus-S | None | 36 | 0 |
| Cerberus-S | Cripto$^a$ | 40 | 8.3 |

$^a$Two-day-old EBs treated with 10 μg/ml of recombinant Cripto for 3 days.

REFERENCES

Adamson, E. D., Minchiotti, G., and Salomon, D. S. (2002). J. Cell. Physiol. 190, 267-278.
Arenas E. (2002). Mol Cell Neurosci 21(2): 205-202.
Bianco, C., et al. (2002). Mol. Cell. Biol. 22, 2586-2597.
Bianco, C., et al. (1999). J. Biol. Chem. 274, 8624-8629.
Brivanlou, A. H., F. H. et al. 2003. Science. 300:913-6.
Bjorklund L. M., et al. (2002). PNAS 99: 2344-2349.
Boheler, K. R., et al. (2002). Circ. Res. 91, 189-201.
Chang, H., et al. (1999) Development 126, 1631-1642.
Cheng, S. K., et al. (2003). Genes Dev. 17, 31-36.
Ciccodicola, A., et al. (1989). EMBO J. 8: 1987-1991
David, N. B., and Rosa, F. M. (2001). Development 128, 3937-3947.
Ding, J., et al. (1998). Nature 395, 702-707.
Doetschman, T., et al. (1993). Hypertension 22, 618-629.
Dono, R., et al. (1993). Development 118, 1157-1168.
Fishman, M. C., and Chien, K. R. (1997). Development 124, 2099-2117.
Galvin, K. M., et al. (2000). Nat. Genet. 24, 171-174.
Gepstein, L. (2002). Circ. Res. 91, 866-876.
Gritsman, K., et al. (1999). Cell 97, 121-132.
Hara A, et al. (2004). Brain Res. 5, 216-21.
Hynes, M., and A. Rosenthal. 2000. Neuron. 28:11-4.
Keller, G. M. (1995). Curr. Opin. Cell. Biol. 7, 862-869.
Laemmli, U. K. (1970). Nature 227, 680-685.
Liu, S., Y. et al. 2000. Proc Natl Acad Sci USA. 97:6126-31.
Lohmeyer, M., et al. (1997). Biochemistry 36, 3837-3845.
Maglione, D., et al. (1991). Proc. Natl. Acad. Sci. USA 88, 9267-9271.
Maltsev, V. A., et al. (1993). Mechanism of Development 44, 41-50.
Marvin, M. J., et al. (2001). Genes Dev. 15, 316-327.
McFadden, D. G., and Olson, E. N. (2002). Current Opinon in Genetics and Development 12, 328-335.
Min, J. Y., et al. 2002. J Appl Physiol. 92:288-96.
Minchiotti, G., et al. (2001). Development 128, 4501-4510.
Minchiotti, G., Parisi, S., Liguori, G., Signore, M., Lania, G., Adamson, E. D., Lago, C. T., and Persico, M. G. (2000). Mech. Dev. 90, 133-142.
Monzen, K., et al. (2001). J. Cell Biol. 153, 687-698.
Monzen, K., Nagai, R., and Komuro, I. (2002). Trends Cardiovasc. Med. 12, 263.
Nagy A, et al. Proc Natl Acad Sci USA (1993) September 15; 90(18):8424-8.
Niwa, H., Yamamura, K., and Miyazaki, J. (1991). Gene 108, 193-199.
Olson, E. N., and Srivastava, D. (1996). Science 272, 671-676.
Piccolo, S., et al. (1999). Nature. 397:707-10.
Reissmann, E., et al. (2001). Genes Dev. 15, 2010-2022.

Reiter, J. F., Verkade, H., and Stainier, D. Y. (2001). Dev. Biol. 234, 330-338.

Renucci, A., Lemarchandel, V., and Rosa, F. (1996). Development 122, 3735-3743.

Rosa, F. M. (2002). Sci. STKE 2002, PE47

Rosenthal, N., and Xavier-Neto, J. (2000). Curr. Opin. Cell Biol. 12, 742-746.

Salomon, D. S., Bianco, C., and De Santis, M. (1999). Bioessays 21, 61-70.

Schiffer, S. G., et al. (2001). J. Biol. Chem. 276, 37769-37778.

Schultheiss, T. M., Burch, J. B., and Lassar, A. B. (1997). Genes Dev. 11, 451-462.

Shen, M. M., and Schier, A. F. (2000). Trends Genet. 16, 303-309.

Smith T. A. and Hooper M. C. (1983). Exp Cell Res 145: 458-62.

Soprano, D. R., and K. J. Soprano. 1995. *Annu Rev Nutr.* 15:111-32.

Sucov, H. M., and R. M. Evans. 1995. *Mol Neurobiol.* 10:169-84.

Svendsen, C. N., and A. G. Smith. 1999. *Trends Neurosci.* 22:357-64.

Tzahor, E., and Lassar, A. B. (2001). Genes Dev. 15, 255-260.

Wieser, R., Wrana, J. L., and Massague, J. (1995). EMBO J. 14, 2199-2208.

Wobus, A. M., Wallukat, G., and Hesheler, J. (1991). Differentiation 48, 173-182.

Xu, C., et al. (1998). Dev. Biol. 196, 237-247.1

Xu, C., et al. (1999). Development 126, 483-494.

Yan, Y. T., et al. (2002). Mol. Cell. Biol. 22, 4439-4449.

Yeo, C., and Whitman, M. (2001). Mol. Cell 7, 949-957.

The invention claimed is:

1. An in vitro method to induce differentiation of a stem cell into a cardiomyocyte, wherein the stem cell is exposed for a period of time and in effective amounts to a soluble form of the Cripto protein, which Cripto protein comprises at least an EGF domain and a CFC domain, and wherein exposure is not achieved by genetic expression of the Cripto protein in the stem cell.

2. The in vitro method according to claim 1 in which the C-terminal hydrophobic terminus of the soluble form of the Cripto protein is replaced by a His tag sequence.

3. The in vitro method according to claim 1 in which the EGF and CFC domains derive from the sequence of human Cripto protein.

4. The in vitro method according to claim 1 in which the EGF and CFC domains derive from the sequence of mouse Cripto protein.

* * * * *